United States Patent
Donovan et al.

(10) Patent No.: US 9,567,575 B2
(45) Date of Patent: Feb. 14, 2017

(54) **PHAGE TWORT ENDOLYSIN CHAP DOMAIN IS LYTIC FOR *STAPHYLOCOCCUS AUREUS***

(71) Applicant: The United States of America, as Represented by the Secretary of Agriculture, Washington, DC (US)

(72) Inventors: David M. Donovan, Baltimore, MD (US); Igor V. Abaev, Obolensk (UA)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 185 days.

(21) Appl. No.: 14/500,273

(22) Filed: Sep. 29, 2014

(65) Prior Publication Data

US 2016/0090584 A1 Mar. 31, 2016

(51) Int. Cl.
*C12N 9/80* (2006.01)
*C12N 15/00* (2006.01)

(52) U.S. Cl.
CPC .......... *C12N 9/80* (2013.01); *C12Y 305/01028* (2013.01)

(58) Field of Classification Search
None
See application file for complete search history.

(56) References Cited

PUBLICATIONS

Loessner et al. (FEMS Microbiology Letters 162 (1998) 265-274).*

* cited by examiner

*Primary Examiner* — Suzanne M Noakes
*Assistant Examiner* — Jae W Lee
(74) *Attorney, Agent, or Firm* — Evelyn M. Rabin; John D. Fado

(57) ABSTRACT

Increases in antibiotic resistant strains of *Staphylococcus aureus* have elicited efforts to develop novel antimicrobials. One potential treatment includes lytic enzymes produced by staphylococcal bacteriophage during the lytic cycle. The phage Twort endolysin (PlyTW) harbors three domains, a CHAP endopeptidase, an amidase-2 domain, and a SH3b-5 cell wall binding domain. The CHAP domain alone is necessary and sufficient for lysis of live *S. aureus*; the amidase-2 domain alone is insufficient. Loss of the SH3b cell wall binding domain results in a 10 fold reduction of enzymatic activity in turbidity reduction and plate lysis assays compared to the full length protein. Deletion of the amidase-2 domain resulted in a protein (PlyTW Δ172-373) with lytic activity that exceeded the activity of the full length construct in both assays. Addition of $Ca^{2+}$ enhanced activity in turbidity reduction assays. Chelation by the addition of EDTA or zinc inhibited the activity of all PlyTW constructs.

11 Claims, 5 Drawing Sheets

SEQUENCE LISTING

<160> NUMBER OF SEQ ID NOS: 47

<210> SEQ ID NO 1
<211> LENGTH: 1428
<212> TYPE: DNA
<213> ORGANISM: Unknown
<220> FEATURE:
<223> OTHER INFORMATION: Phage or Bacteriophage  TWORT     PlyTW

<400> SEQUENCE: 1

```
atgaaaaccc tgaaacaagc agagtcctac attaagagta agtaaatac aggaactgat      60
tttgatggtt tatatgggta tcagtgtatg gacttagcag tagattatat ttaccatgta     120
acagatggta aaataagaat gtggggtaat gctaaggatg cgataaataa ctcttttggt     180
ggtactgcta cggtatataa aaactaccct gcttttagac ctaagtacgg tgatgtagtc     240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420
agacctaact ttgctactga atcaagtgta aaaaagaaag atacaaagaa aaaaccaaaa    480
ccatcaaata gagatggaat aaataaagat aaaattgtat atgatagaac taatattaat    540
tacaatatgg ttaaacgagg atataatcct gtaggtgtaa tttacacaa cgatgctgga    600
agtatgacag gattacagta taaaaataat ttgcaaaatg cgggatataa ccgatgggct    660
caaggtatag ctcactcata tatttctgaa ggtcaagtat ggcaagcctt aggagaaagt    720
cgtatagctt ggcattgtgc taatcagtgg ggaaataaaa accttatgg tattgaaata     780
tgccaatcaa tgactgcatc tgatgagcaa tttcttaaaa atgaacaaac agcgttttat    840
gaggcatcac gtatgcttaa aaaatgggga ctaaagccag ataaaaatac agtacgacta    900
catatggaat attaccaaac tgcatgtcct catcgctcta tgaagttgca tgtaggtaaa    960
gaccctacta aaacttctat cactcaggct gatatagaaa aacttaaaga atattttatt   1020
aaacaaatta aaatgtatta tgaaggtaaa acaccagtac caacagtagt aaatcaaaaa   1080
gccaaaacaa aaccagttaa gcagtcaagt acaagtggat ggaacgttaa taattatggt   1140
acttactata aatccgagag cgctacgttt aagtgtacag cacgtcaagg tatcgttaca   1200
cgatatactg gacctttac tacgtgtcct caagcaggag tactatatta tggtcaatct    1260
gtaacttatg atacggtttg taagcaagat ggttatgtat ggattagttg gactactaat   1320
ggaggtcaag atgtttggat gcctgtaaga acatgggata aaaacacaga cattatgggt   1380
cagctatggg gagatatata tctcgagcac caccaccacc accactga                1428
```

<210> SEQ ID NO 2
<211> LENGTH: 475
<212> TYPE: PRT
<213> ORGANISM: Unknown
<220> FEATURE:
<223> OTHER INFORMATION: Phage or Bacteriophage  TWORT     PlyTW

<400> SEQUENCE: 2

```
Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45
```

```
Gly Asn Ala Lys Asp Ala Ile Asn Asn Ser Phe Gly Gly Thr Ala Thr
     50                  55                  60

Val Tyr Lys Asn Tyr Pro Ala Phe Arg Pro Lys Tyr Gly Asp Val Val
 65              70                  75                  80

Val Trp Thr Thr Gly Asn Phe Ala Thr Tyr Gly His Ile Ala Ile Val
                 85                  90                  95

Thr Asn Pro Asp Pro Tyr Gly Asp Leu Gln Tyr Val Thr Val Leu Glu
             100                 105                 110

Gln Asn Trp Asn Gly Asn Gly Ile Tyr Lys Thr Glu Leu Ala Thr Ile
             115                 120                 125

Arg Thr His Asp Tyr Thr Gly Ile Thr His Phe Ile Arg Pro Asn Phe
         130                 135                 140

Ala Thr Glu Ser Ser Val Lys Lys Asp Thr Lys Lys Pro Lys
145                 150                 155                 160

Pro Ser Asn Arg Asp Gly Ile Asn Lys Asp Lys Ile Val Tyr Asp Arg
                 165                 170                 175

Thr Asn Ile Asn Tyr Asn Met Val Lys Arg Gly Tyr Asn Pro Val Gly
             180                 185                 190

Val Ile Leu His Asn Asp Ala Gly Ser Met Thr Gly Leu Gln Tyr Lys
             195                 200                 205

Asn Asn Leu Gln Asn Ala Gly Tyr Asn Arg Trp Ala Gln Gly Ile Ala
210                 215                 220

His Ser Tyr Ile Ser Glu Gly Gln Val Trp Gln Ala Leu Gly Glu Ser
225                 230                 235                 240

Arg Ile Ala Trp His Cys Ala Asn Gln Trp Gly Asn Lys Asn Leu Tyr
                 245                 250                 255

Gly Ile Glu Ile Cys Gln Ser Met Thr Ala Ser Asp Glu Gln Phe Leu
             260                 265                 270

Lys Asn Glu Gln Thr Ala Phe Tyr Glu Ala Ser Arg Met Leu Lys Lys
             275                 280                 285

Trp Gly Leu Lys Pro Asp Lys Asn Thr Val Arg Leu His Met Glu Tyr
290                 295                 300

Tyr Gln Thr Ala Cys Pro His Arg Ser Met Lys Leu His Val Gly Lys
305                 310                 315                 320

Asp Pro Thr Lys Thr Ser Ile Thr Gln Ala Asp Ile Glu Lys Leu Lys
                 325                 330                 335

Glu Tyr Phe Ile Lys Gln Ile Lys Met Tyr Tyr Glu Gly Lys Thr Pro
             340                 345                 350

Val Pro Thr Val Val Asn Gln Lys Ala Lys Thr Lys Pro Val Lys Gln
             355                 360                 365

Ser Ser Thr Ser Gly Trp Asn Val Asn Asn Tyr Gly Thr Tyr Tyr Lys
370                 375                 380

Ser Glu Ser Ala Thr Phe Lys Cys Thr Ala Arg Gln Gly Ile Val Thr
385                 390                 395                 400

Arg Tyr Thr Gly Pro Phe Thr Thr Cys Pro Gln Ala Gly Val Leu Tyr
                 405                 410                 415

Tyr Gly Gln Ser Val Thr Tyr Asp Thr Val Cys Lys Gln Asp Gly Tyr
             420                 425                 430

Val Trp Ile Ser Trp Thr Thr Asn Gly Gly Gln Asp Val Trp Met Pro
             435                 440                 445

Val Arg Thr Trp Asp Lys Asn Thr Asp Ile Met Gly Gln Leu Trp Gly
450                 455                 460

Asp Ile Tyr Leu Glu His His His His His
```

<210> SEQ ID NO 3
<211> LENGTH: 465
<212> TYPE: DNA
<213> ORGANISM: Unknown
<220> FEATURE:
<223> OTHER INFORMATION: Phage or Bacteriophage  TWORT    PlyTW

<400> SEQUENCE: 3

```
atgaaaaccc tgaaacaagc agagtcctac attaagagta aagtaaatac aggaactgat    60
tttgatggtt tatatgggta tcagtgtatg gacttagcag tagattatat ttaccatgta   120
acagatggta aataagaat gtggggtaat gctaaggatg cgataaataa ctcttttggt   180
ggtactgcta cggtatataa aaactaccct gcttttagac ctaagtacgg tgatgtagtc   240
gtatggacta ctggtaattt tgcaacttat ggtcatatcg caatagttac taaccctgac   300
ccttatggag accttcaata tgttacagtt cttgaacaaa actggaacgg taacgggatt   360
tataaaaccg agttagctac aatcagaaca cacgattaca caggaattac acatttatt   420
agacctaact ttgctactct cgagcaccac caccaccacc actga   465
```

<210> SEQ ID NO 4
<211> LENGTH: 154
<212> TYPE: PRT
<213> ORGANISM: Unknown
<220> FEATURE:
<223> OTHER INFORMATION: Phage or Bacteriophage  TWORT    PlyTW

<400> SEQUENCE: 4

```
Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Leu Glu His His His His His His
145                 150
```

<210> SEQ ID NO 5
<211> LENGTH: 543
<212> TYPE: DNA
<213> ORGANISM: Unknown
<220> FEATURE:
<223> OTHER INFORMATION: Phage or Bacteriophage  TWORT    PlyTW

<400> SEQUENCE: 5

```
atgaaaaccc tgaaacaagc agagtcctac attaagagta aagtaaatac aggaactgat    60
```

```
tttgatggtt tatatgggta tcagtgtatg gacttagcag tagattatat ttaccatgta      120
acagatggta aaataagaat gtggggtaat gctaaggatg cgataaataa ctcttttggt      180
ggtactgcta cggtatataa aaactacccct gcttttagac ctaagtacgg tgatgtagtc     240
gtatggacta ctggtaattt tgcaacttat ggtcatatcg caatagttac taaccctgac      300
ccttatggag accttcaata tgttacagtt cttgaacaaa actggaacgg taacgggatt      360
tataaaaccg agttagctac aatcagaaca cacgattaca caggaattac acattttatt     420
agacctaact ttgctactga atcaagtgta aaaagaaag atacaaagaa aaaaccaaaa      480
ccatcaaata gagatggaat aaataaagat aaaattctcg agcaccacca ccaccaccac     540
tga                                                                   543

<210> SEQ ID NO 6
<211> LENGTH: 180
<212> TYPE: PRT
<213> ORGANISM: Unknown
<220> FEATURE:
<223> OTHER INFORMATION: Phage or Bacteriophage  TWORT    PlyTW

<400> SEQUENCE: 6

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Asp Thr Lys Lys Pro Lys
145                 150                 155                 160

Pro Ser Asn Arg Asp Gly Ile Asn Lys Asp Lys Ile Leu Glu His His
                165                 170                 175

His His His His
            180

<210> SEQ ID NO 7
<211> LENGTH: 591
<212> TYPE: DNA
<213> ORGANISM: Unknown
<220> FEATURE:
<223> OTHER INFORMATION: Phage or Bacteriophage  TWORT    PlyTW

<400> SEQUENCE: 7
atgaaaaccc tgaaacaagc agagtcctac attaagagta agtaaatac aggaactgat       60 tttgatggtt tatatgggta tcagtgtatg gacttagcag tagattatat ttaccatgta     120
```

```
acagatggta aaataagaat gtggggtaat gctaaggatg cgataaataa ctcttttggt      180
ggtactgcta cggtatataa aaactacccct gcttttagac ctaagtacgg tgatgtagtc     240
gtatggacta ctggtaattt tgcaacttat ggtcatatcg caatagttac taaccctgac     300
ccttatggag accttcaata tgttacagtt cttgaacaaa actggaacgg taacgggatt     360
tataaaaccg agttagctac aatcagaaca cacgattaca caggaattac acattttatt     420
agacctaact tgctactga atcaagtgta aaaagaaag atacaaagaa aaaccaaaa         480 ccatcaaata gagatggaat aaataaagat aaaattgtat atgatagaac taatattaat     540
tacaatatgg ttaaacgagg atatctcgag caccaccacc accaccactg a               591
```

```
<210> SEQ ID NO 8
<211> LENGTH: 196
<212> TYPE: PRT
<213> ORGANISM: Unknown
<220> FEATURE:
<223> OTHER INFORMATION: Phage or Bacteriophage  TWORT   PlyTW

<400> SEQUENCE: 8

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Asp Thr Lys Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Leu Glu His His
            180                 185                 190

His His His His
        195
```

```
<210> SEQ ID NO 9
<211> LENGTH: 624
<212> TYPE: DNA
<213> ORGANISM: Unknown
<220> FEATURE:
<223> OTHER INFORMATION: Phage or Bacteriophage  TWORT   PlyTW

<400> SEQUENCE: 9
atgaaaaccc tgaaacaagc agagtcctac attaagagta agtaaatac aggaactgat       60 tttgatggtt tatatgggta tcagtgtatg gacttagcag tagattatat ttaccatgta     120
```

```
acagatggta aaataagaat gtggggtaat gctaaggatg cgataaataa ctcttttggt      180
ggtactgcta cggtatataa aaactacccct gcttttagac ctaagtacgg tgatgtagtc     240
gtatggacta ctggtaattt tgcaacttat ggtcatatcg caatagttac taaccctgac     300
ccttatggag accttcaata tgttacagtt cttgaacaaa actggaacgg taacgggatt     360
tataaaaccg agttagctac aatcagaaca cacgattaca caggaattac acattttatt     420
agacctaact ttgctactga atcaagtgta aaaagaaag  atacaaagaa aaaaccaaaa     480
ccatcaaata gagatggaat aaataaagat aaaattgtat atgatagaac taatattaat     540
tacaatatgg ttaaacgagg atataatcct gtaggtgtaa ttttacacaa cgatgctctc     600
gagcaccacc accaccacca ctga                                            624
```

<210> SEQ ID NO 10
<211> LENGTH: 207
<212> TYPE: PRT
<213> ORGANISM: Unknown
<220> FEATURE:
<223> OTHER INFORMATION: Phage or Bacteriophage TWORT PlyTW

<400> SEQUENCE: 10

```
Met Lys Thr Leu Lys Gln Ala Glu Ser Tyr Ile Lys Ser Lys Val Asn
 1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Lys Asp Thr Lys Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Leu Glu His His His His His His
        195                 200                 205
```

<210> SEQ ID NO 11
<211> LENGTH: 762
<212> TYPE: DNA
<213> ORGANISM: Unknown
<220> FEATURE:
<223> OTHER INFORMATION: Phage or Bacteriophage TWORT PlyTW

<400> SEQUENCE: 11

```
atgaaaaccc tgaaacaagc agagtcctac attaagagta agtaaatac aggaactgat    60
```

-continued

```
tttgatggtt tatatgggta tcagtgtatg gacttagcag tagattatat ttaccatgta    120
acagatggta aaataagaat gtggggtaat gctaaggatg cgataaataa ctcttttggt    180
ggtactgcta cggtatataa aaactaccct gcttttagac ctaagtacgg tgatgtagtc    240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420
agacctaact ttgctactga atcaagtgta aaaagaaag atacaaagaa aaaccaaaa     480 ccatcaaata gagatggaat aaataaagat aaaattgtat atgatagaac taatattaat    540
tacaatatgg ttaaacgagg atataatcct gtaggtgtaa ttttacacaa cgatgctgga    600
agtatgacag gattacagta taaaaataat ttgcaaaatg cgggatataa ccgatgggct    660
caaggtatag ctcactcata tatttctgaa ggtcaagtat ggcaagcctt aggagaaagt    720
cgtatagctt ggcatctcga gcaccaccac caccaccact ga                     762
```

<210> SEQ ID NO 12
<211> LENGTH: 253
<212> TYPE: PRT
<213> ORGANISM: Unknown
<220> FEATURE:
<223> OTHER INFORMATION: Phage or Bacteriophage TWORT PlyTW

<400> SEQUENCE: 12

```
Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Lys Asp Thr Lys Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Gly Ser Met Thr Gly Leu Gln Tyr Lys
        195                 200                 205

Asn Asn Leu Gln Asn Ala Gly Tyr Asn Arg Trp Ala Gln Gly Ile Ala
    210                 215                 220

His Ser Tyr Ile Ser Glu Gly Gln Val Trp Gln Ala Leu Gly Glu Ser
225                 230                 235                 240
```

Arg Ile Ala Trp His Leu Glu His His His His His
              245                 250

<210> SEQ ID NO 13
<211> LENGTH: 996
<212> TYPE: DNA
<213> ORGANISM: Unknown
<220> FEATURE:
<223> OTHER INFORMATION: Phage or Bacteriophage  TWORT    PlyTW

<400> SEQUENCE: 13

```
atgaaaaccc tgaaacaagc agagtcctac attaagagta agtaaatac aggaactgat      60
tttgatggtt tatatgggta tcagtgtatg gacttagcag tagattatat ttaccatgta    120
acagatggta aaataagaat gtggggtaat gctaaggatg cgataaataa ctcttttggt    180
ggtactgcta cggtatataa aaactaccct gcttttagac ctaagtacgg tgatgtagtc    240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acatttatt    420
agacctaact ttgctactga atcaagtgta aaaagaaag atacaaagaa aaaaccaaaa    480
ccatcaaata gagatggaat aaataaagat aaaattgtat atgatagaac taatattaat    540
tacaatatgg ttaaacgagg atataatcct gtaggtgtaa ttttacacaa cgatgctgga    600
agtatgacag gattacagta taaaaataat ttgcaaaatg cgggatataa ccgatgggct    660
caaggtatag ctcactcata tatttctgaa ggtcaagtat ggcaagcctt aggagaaagt    720
cgtatagctt ggcattgtgc taatcagtgg ggaaataaaa acctttatgg tattgaaata    780
tgccaatcaa tgactgcatc tgatgagcaa tttcttaaaa atgaacaaac agcgttttat    840
gaggcatcac gtatgcttaa aaaatgggga ctaaagccag ataaaaatac agtacgacta    900
catatggaat attaccaaac tgcatgtcct catcgctcta tgaagttgca tgtaggtaaa    960
gaccctactc tcgagcacca ccaccaccac cactga                              996
```

<210> SEQ ID NO 14
<211> LENGTH: 331
<212> TYPE: PRT
<213> ORGANISM: Unknown
<220> FEATURE:
<223> OTHER INFORMATION: Phage or Bacteriophage  TWORT    PlyTW

<400> SEQUENCE: 14

Met Lys Thr Leu Lys Gln Ala Glu Ser Tyr Ile Lys Ser Lys Val Asn
 1               5                  10                  15

Thr Gly Thr Asp Phe Asp Gly Leu Tyr Gly Tyr Gln Cys Met Asp Leu
                20                  25                  30

Ala Val Asp Tyr Ile Tyr His Val Thr Asp Gly Lys Ile Arg Met Trp
            35                  40                  45

Gly Asn Ala Lys Asp Ala Ile Asn Asn Ser Phe Gly Gly Thr Ala Thr
        50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile

```
              115                 120                 125
Arg Thr His Asp Tyr Thr Gly Ile Thr His Phe Ile Arg Pro Asn Phe
    130                 135                 140

Ala Thr Glu Ser Ser Val Lys Lys Asp Thr Lys Lys Pro Lys
145                 150                 155                 160

Pro Ser Asn Arg Asp Gly Ile Asn Lys Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Gly Ser Met Thr Gly Leu Gln Tyr Lys
        195                 200                 205

Asn Asn Leu Gln Asn Ala Gly Tyr Asn Arg Trp Ala Gln Gly Ile Ala
    210                 215                 220

His Ser Tyr Ile Ser Glu Gly Gln Val Trp Gln Ala Leu Gly Glu Ser
225                 230                 235                 240

Arg Ile Ala Trp His Cys Ala Asn Gln Trp Gly Asn Lys Asn Leu Tyr
                245                 250                 255

Gly Ile Glu Ile Cys Gln Ser Met Thr Ala Ser Asp Glu Gln Phe Leu
            260                 265                 270

Lys Asn Glu Gln Thr Ala Phe Tyr Glu Ala Ser Arg Met Leu Lys Lys
        275                 280                 285

Trp Gly Leu Lys Pro Asp Lys Asn Thr Val Arg Leu His Met Glu Tyr
    290                 295                 300

Tyr Gln Thr Ala Cys Pro His Arg Ser Met Lys Leu His Val Gly Lys
305                 310                 315                 320

Asp Pro Thr Leu Glu His His His His His His
                325                 330

<210> SEQ ID NO 15
<211> LENGTH: 1155
<212> TYPE: DNA
<213> ORGANISM: Unknown
<220> FEATURE:
<223> OTHER INFORMATION: Phage or Bacteriophage  TWORT    PlyTW

<400> SEQUENCE: 15
atgaaaaccc tgaaacaagc agagtcctac attaagagta agtaaatac aggaactgat      60 tttgatggtt tatatgggta tcagtgtatg gacttagcag tagattatat ttaccatgta    120
acagatggta aaataagaat gtggggtaat gctaaggatg cgataaataa ctcttttggt    180
ggtactgcta cggtatataa aaactcccct gcttttagac ctaagtacgg tgatgtagtc    240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420
agacctaact tgctactga atcaagtgta aaaagaaag atacaaagaa aaaaccaaaa      480
ccatcaaata gagatggaat aaataaagat aaaattgtat atgatagaac taatattaat    540
tacaatatgg ttaaacgagg atataatcct gtaggtgtaa ttttacacaa cgatgctgga    600
agtatgacag gattacagta taaaaataat ttgcaaaatg cgggatataa ccgatgggct    660
caaggtatag ctcactcata tatttctgaa ggtcaagtat ggcaagcctt aggagaaagt    720
cgtatagctt ggcattgtgc taatcagtgg ggaaataaaa accttatggg tattgaaata    780
tgccaatcaa tgactgcatc tgatgagcaa tttcttaaaa atgaacaaac agcgtttat     840
```

```
gaggcatcac gtatgcttaa aaaatgggga ctaaagccag ataaaaatac agtacgacta    900
catatggaat attaccaaac tgcatgtcct catcgctcta tgaagttgca tgtaggtaaa    960
gaccctacta aaacttctat cactcaggct gatatagaaa aacttaaaga atattttatt   1020
aaacaaatta aaatgtatta tgaaggtaaa acaccagtac caacagtagt aaatcaaaaa   1080
gccaaaacaa aaccagttaa gcagtcaagt acaagtggat ggaacgttct cgagcaccac   1140
caccaccacc actga                                                   1155
```

<210> SEQ ID NO 16
<211> LENGTH: 384
<212> TYPE: PRT
<213> ORGANISM: Unknown
<220> FEATURE:
<223> OTHER INFORMATION: Phage or Bacteriophage  TWORT    PlyTW

<400> SEQUENCE: 16

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
                20                  25                  30

Ala Val Asp Tyr Ile Tyr His Val Thr Asp Gly Lys Ile Arg Met Trp
            35                  40                  45

Gly Asn Ala Lys Asp Ala Ile Asn Asn Ser Phe Gly Gly Thr Ala Thr
        50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
130                 135                 140

Ala Thr Glu Ser Ser Val Lys Lys Lys Asp Thr Lys Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Gly Ser Met Thr Gly Leu Gln Tyr Lys
        195                 200                 205

Asn Asn Leu Gln Asn Ala Gly Tyr Asn Arg Trp Ala Gln Gly Ile Ala
    210                 215                 220

His Ser Tyr Ile Ser Glu Gly Gln Val Trp Gln Ala Leu Gly Glu Ser
225                 230                 235                 240

Arg Ile Ala Trp His Cys Ala Asn Gln Trp Gly Asn Lys Asn Leu Tyr
                245                 250                 255

Gly Ile Glu Ile Cys Gln Ser Met Thr Ala Ser Asp Glu Gln Phe Leu
            260                 265                 270

Lys Asn Glu Gln Thr Ala Phe Tyr Glu Ala Ser Arg Met Leu Lys Lys
        275                 280                 285

Trp Gly Leu Lys Pro Asp Lys Asn Thr Val Arg Leu His Met Glu Tyr
    290                 295                 300

Tyr Gln Thr Ala Cys Pro His Arg Ser Met Lys Leu His Val Gly Lys
305                 310                 315                 320

Asp Pro Thr Lys Thr Ser Ile Thr Gln Ala Asp Ile Glu Lys Leu Lys
                325                 330                 335

Glu Tyr Phe Ile Lys Gln Ile Lys Met Tyr Tyr Glu Gly Lys Thr Pro
            340                 345                 350

Val Pro Thr Val Val Asn Gln Lys Ala Lys Thr Lys Pro Val Lys Gln
        355                 360                 365

Ser Ser Thr Ser Gly Trp Asn Val Leu Glu His His His His His
        370                 375                 380

<210> SEQ ID NO 17
<211> LENGTH: 1203
<212> TYPE: DNA
<213> ORGANISM: Unknown
<220> FEATURE:
<223> OTHER INFORMATION: Phage or Bacteriophage  TWORT   PlyTW

<400> SEQUENCE: 17
atgaaaaccc tgaaacaagc agagtcctac attaagagta agtaaatac aggaactgat        60 tttgatggtt tatatgggta tcagtgtatg gacttagcag tagattatat ttaccatgta      120
acagatggta aaataagaat gtggggtaat gctaaggatg cgataaataa ctcttttggt      180
ggtactgcta cggtatataa aaactaccct gcttttagac ctaagtacgg tgatgtagtc      240
gtatggacta ctggtaattt tgcaacttat ggtcatatcg caatagttac taaccctgac      300
ccttatggag accttcaata tgttacagtt cttgaacaaa actggaacgg taacgggatt      360
tataaaaccg agttagctac aatcagaaca cacgattaca caggaattac acatttta t      420 agacctaact tgctactga atcaagtgta aaaagaaag atacaaagaa aaaaccaaaa       480
ccatcaaata gagatggaat aaataaagat aaaattgtat atgatagaac taatattaat      540
tacaatatgg ttaaacgagg atataatcct gtaggtgtaa tttacacaa cgatgctgga       600 agtatgacag gattacagta taaaaataat ttgcaaaatg cgggatataa ccgatgggct      660
caaggtatag ctcactcata tatttctgaa ggtcaagtat ggcaagcctt aggagaaagt      720
cgtatagctt ggcattgtgc taatcagtgg ggaaataaaa acctttatgg tattgaaata      780
tgccaatcaa tgactgcatc tgatgagcaa tttcttaaaa atgaacaaac agcgttttat      840
gaggcatcac gtatgcttaa aaaatgggga ctaaagccag ataaaaatac agtacgacta      900
catatggaat attaccaaac tgcatgtcct catcgctcta tgaagttgca tgtaggtaaa      960
gaccctacta aaacttctat cactcaggct gatatagaaa aacttaaaga atattttatt     1020
aaacaaatta aatgtatta tgaaggtaaa acaccagtac caacagtagt aaatcaaaaa      1080
gccaaaacaa aaccagttaa gcagtcaagt acaagtggat ggaacgttaa taattatggt     1140
acttactata atccgagag cgctacgttt aagtgtctcg agcaccacca ccaccaccac     1200
tga                                                                   1203

<210> SEQ ID NO 18
<211> LENGTH: 400
<212> TYPE: PRT
<213> ORGANISM: Unknown
<220> FEATURE:
<223> OTHER INFORMATION: Phage or Bacteriophage  TWORT   PlyTW

<400> SEQUENCE: 18

Met Lys Thr Leu Lys Gln Ala Glu Ser Tyr Ile Lys Ser Lys Val Asn
1               5                   10                  15

```
Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
 50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
130                 135                 140

Ala Thr Glu Ser Ser Val Lys Lys Asp Thr Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Gly Ser Met Thr Gly Leu Gln Tyr Lys
        195                 200                 205

Asn Asn Leu Gln Asn Ala Gly Tyr Asn Arg Trp Ala Gln Gly Ile Ala
210                 215                 220

His Ser Tyr Ile Ser Glu Gly Gln Val Trp Gln Ala Leu Gly Glu Ser
225                 230                 235                 240

Arg Ile Ala Trp His Cys Ala Asn Gln Trp Gly Asn Lys Asn Leu Tyr
                245                 250                 255

Gly Ile Glu Ile Cys Gln Ser Met Thr Ala Ser Asp Glu Gln Phe Leu
            260                 265                 270

Lys Asn Glu Gln Thr Ala Phe Tyr Glu Ala Ser Arg Met Leu Lys Lys
        275                 280                 285

Trp Gly Leu Lys Pro Asp Lys Asn Thr Val Arg Leu His Met Glu Tyr
290                 295                 300

Tyr Gln Thr Ala Cys Pro His Arg Ser Met Lys Leu His Val Gly Lys
305                 310                 315                 320

Asp Pro Thr Lys Thr Ser Ile Thr Gln Ala Asp Ile Glu Lys Leu Lys
                325                 330                 335

Glu Tyr Phe Ile Lys Gln Ile Lys Met Tyr Tyr Glu Gly Lys Thr Pro
            340                 345                 350

Val Pro Thr Val Val Asn Gln Lys Ala Lys Thr Lys Pro Val Lys Gln
        355                 360                 365

Ser Ser Thr Ser Gly Trp Asn Val Asn Asn Tyr Gly Thr Tyr Tyr Lys
370                 375                 380

Ser Glu Ser Ala Thr Phe Lys Cys Leu Glu His His His His His
385                 390                 395                 400
```

<210> SEQ ID NO 19
<211> LENGTH: 786
<212> TYPE: DNA
<213> ORGANISM: Unknown
<220> FEATURE:

<223> OTHER INFORMATION: Phage or Bacteriophage TWORT   PlyTW

<400> SEQUENCE: 19

```
atgagaccta actttgctac tgaatcaagt gtaaaaaaga agatacaaa gaaaaaacca      60
aaaccatcaa atagagatgg aataaataaa gataaaattg tatatgatag aactaatatt    120
aattacaata tggttaaacg aggatataat cctgtaggtg taattttaca caacgatgct    180
ggaagtatga caggattaca gtataaaaat aatttgcaaa atgcgggata taaccgatgg    240
gctcaaggta tagctcactc atatatttct gaaggtcaag tatggcaagc cttaggagaa    300
agtcgtatag cttggcattg tgctaatcag tggggaaata aaaaccttta tggtattgaa    360
atatgccaat caatgactgc atctgatgag caatttctta aaaatgaaca aacagcgttt    420
tatgaggcat cacgtatgct taaaaaatgg ggactaaagc cagataaaaa tacagtacga    480
ctacatatgg aatattacca aactgcatgt cctcatcgct ctatgaagtt gcatgtaggt    540
aaagacccta ctaaaacttc tatcactcag gctgatatag aaaaacttaa agaatatttt    600
attaaacaaa ttaaaatgta ttatgaaggt aaaacaccag taccaacagt agtaaatcaa    660
aaagccaaaa caaaaccagt taagcagtca agtacaagtg gatggaacgt taataattat    720
ggtacttact ataaatccga gagcgctacg tttaagtgtc tcgagcacca ccaccaccac    780
cactga                                                               786
```

<210> SEQ ID NO 20
<211> LENGTH: 261
<212> TYPE: PRT
<213> ORGANISM: Unknown
<220> FEATURE:
<223> OTHER INFORMATION: Phage or Bacteriophage TWORT   PlyTW

<400> SEQUENCE: 20

```
Met Arg Pro Asn Phe Ala Thr Glu Ser Ser Val Lys Lys Asp Thr
1               5                   10                  15

Lys Lys Lys Pro Lys Pro Ser Asn Arg Asp Gly Ile Asn Lys Asp Lys
            20                  25                  30

Ile Val Tyr Asp Arg Thr Asn Ile Asn Tyr Asn Met Val Lys Arg Gly
        35                  40                  45

Tyr Asn Pro Val Gly Val Ile Leu His Asn Asp Ala Gly Ser Met Thr
    50                  55                  60

Gly Leu Gln Tyr Lys Asn Asn Leu Gln Asn Ala Gly Tyr Asn Arg Trp
65                  70                  75                  80

Ala Gln Gly Ile Ala His Ser Tyr Ile Ser Glu Gly Gln Val Trp Gln
                85                  90                  95

Ala Leu Gly Glu Ser Arg Ile Ala Trp His Cys Ala Asn Gln Trp Gly
            100                 105                 110

Asn Lys Asn Leu Tyr Gly Ile Glu Ile Cys Gln Ser Met Thr Ala Ser
        115                 120                 125

Asp Glu Gln Phe Leu Lys Asn Glu Gln Thr Ala Phe Tyr Glu Ala Ser
    130                 135                 140

Arg Met Leu Lys Lys Trp Gly Leu Lys Pro Asp Lys Asn Thr Val Arg
145                 150                 155                 160

Leu His Met Glu Tyr Tyr Gln Thr Ala Cys Pro His Arg Ser Met Lys
                165                 170                 175

Leu His Val Gly Lys Asp Pro Thr Lys Thr Ser Ile Thr Gln Ala Asp
            180                 185                 190

Ile Glu Lys Leu Lys Glu Tyr Phe Ile Lys Gln Ile Lys Met Tyr Tyr
```

195                 200                 205
Glu Gly Lys Thr Pro Val Pro Thr Val Val Asn Gln Lys Ala Lys Thr
                    210                 215                 220

Lys Pro Val Lys Gln Ser Ser Thr Ser Gly Trp Asn Val Asn Asn Tyr
225                 230                 235                 240

Gly Thr Tyr Tyr Lys Ser Glu Ser Ala Thr Phe Lys Cys Leu Glu His
                245                 250                 255

His His His His His
            260

<210> SEQ ID NO 21
<211> LENGTH: 753
<212> TYPE: DNA
<213> ORGANISM: Unknown
<220> FEATURE:
<223> OTHER INFORMATION: Phage or Bacteriophage  TWORT   PlyTW

<400> SEQUENCE: 21

```
atgaaaaccc tgaaacaagc agagtcctac attaagagta agtaaatac aggaactgat      60
tttgatggtt tatatgggta tcagtgtatg gacttagcag tagattatat ttaccatgta    120
acagatggta aataagaat gtggggtaat gctaaggatg cgataaataa ctcttttggt    180
ggtactgcta cggtatataa aaactacccct gcttttagac ctaagtacgg tgatgtagtc    240
gtatggacta ctggtaattt tgcaactat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420
agacctaact tgctactct cgactggaac gttaataatt atggtactta ctataaatcc    480
gagagcgcta cgtttaagtg tacagcacgt caaggtatcg ttacacgata tactggacct    540
tttactacgt gtcctcaagc aggagtacta tattatggtc aatctgtaac ttatgatacg    600
gtttgtaagc aagatggtta tgtatggatt agttggacta ctaatggagg tcaagatgtt    660
tggatgcctg taagaacatg ggataaaaac acagacatta tgggtcagct atggggagat    720
atatatctcg agcaccacca ccaccaccac tga                                 753
```

<210> SEQ ID NO 22
<211> LENGTH: 250
<212> TYPE: PRT
<213> ORGANISM: Unknown
<220> FEATURE:
<223> OTHER INFORMATION: Phage or Bacteriophage  TWORT   PlyTW

<400> SEQUENCE: 22

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
                20                  25                  30

Ala Val Asp Tyr Ile Tyr His Val Thr Asp Gly Lys Ile Arg Met Trp
            35                  40                  45

Gly Asn Ala Lys Asp Ala Ile Asn Asn Ser Phe Gly Gly Thr Ala Thr
        50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu

```
                    100                 105                 110
Gln Asn Trp Asn Gly Asn Gly Ile Tyr Lys Thr Glu Leu Ala Thr Ile
            115                 120                 125

Arg Thr His Asp Tyr Thr Gly Ile Thr His Phe Ile Arg Pro Asn Phe
    130                 135                 140

Ala Thr Leu Asp Trp Asn Val Asn Asn Tyr Gly Thr Tyr Tyr Lys Ser
145                 150                 155                 160

Glu Ser Ala Thr Phe Lys Cys Thr Ala Arg Gln Gly Ile Val Thr Arg
                165                 170                 175

Tyr Thr Gly Pro Phe Thr Thr Cys Pro Gln Ala Gly Val Leu Tyr Tyr
            180                 185                 190

Gly Gln Ser Val Thr Tyr Asp Thr Val Cys Lys Gln Asp Gly Tyr Val
        195                 200                 205

Trp Ile Ser Trp Thr Thr Asn Gly Gly Gln Asp Val Trp Met Pro Val
    210                 215                 220

Arg Thr Trp Asp Lys Asn Thr Asp Ile Met Gly Gln Leu Trp Gly Asp
225                 230                 235                 240

Ile Tyr Leu Glu His His His His His His
                245                 250

<210> SEQ ID NO 23
<211> LENGTH: 831
<212> TYPE: DNA
<213> ORGANISM: Unknown
<220> FEATURE:
<223> OTHER INFORMATION: Phage or Bacteriophage   TWORT     PlyTW

<400> SEQUENCE: 23
atgaaaaccc tgaaacaagc agagtcctac attaagagta agtaaatac aggaactgat      60 tttgatggtt tatatgggta tcagtgtatg gacttagcag tagattatat ttaccatgta    120
acagatggta aaataagaat gtggggtaat gctaaggatg cgataaataa ctctttttggt   180 ggtactgcta cggtatataa aaactacccct gcttttagac ctaagtacgg tgatgtagtc   240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420
agacctaact ttgctactga atcaagtgta aaaaagaaag atacaaagaa aaaaccaaaa    480
ccatcaaata gagatggaat aaataaagat aaaattctcg actggaacgt taataattat    540
ggtacttact ataatccgga gagcgctacg tttaagtgta cagcacgtca aggtatcgtt    600
acacgatata ctggaccttt tactacgtgt cctcaagcag gagtactata ttatggtcaa    660
tctgtaacct tatgatacggt tgtaagcaa gatggttatg tatggattag ttggactact    720
aatggaggtc aagatgtttg gatgcctgta agaacatggg ataaaaacac agacattatg    780
ggtcagctat gggagatat atatctcgag caccaccacc accaccactg a             831

<210> SEQ ID NO 24
<211> LENGTH: 276
<212> TYPE: PRT
<213> ORGANISM: Unknown
<220> FEATURE:
<223> OTHER INFORMATION: Phage or Bacteriophage   TWORT     PlyTW

<400> SEQUENCE: 24

Met Lys Thr Leu Lys Gln Ala Glu Ser Tyr Ile Lys Ser Lys Val Asn
1               5                   10                  15
```

Thr Gly Thr Asp Phe Asp Gly Leu Tyr Gly Tyr Gln Cys Met Asp Leu
         20                  25                  30

Ala Val Asp Tyr Ile Tyr His Val Thr Asp Gly Lys Ile Arg Met Trp
         35                  40                  45

Gly Asn Ala Lys Asp Ala Ile Asn Asn Ser Phe Gly Gly Thr Ala Thr
 50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Tyr Gly His Ile Ala Ile Val
                 85                  90                  95

Thr Asn Pro Asp Pro Tyr Gly Asp Leu Gln Tyr Val Thr Val Leu Glu
             100                 105                 110

Gln Asn Trp Asn Gly Asn Gly Ile Tyr Lys Thr Glu Leu Ala Thr Ile
             115                 120                 125

Arg Thr His Asp Tyr Thr Gly Ile Thr His Phe Ile Arg Pro Asn Phe
         130                 135                 140

Ala Thr Glu Ser Ser Val Lys Lys Lys Asp Thr Lys Lys Lys Pro Lys
145                 150                 155                 160

Pro Ser Asn Arg Asp Gly Ile Asn Lys Asp Lys Ile Leu Asp Trp Asn
                 165                 170                 175

Val Asn Asn Tyr Gly Thr Tyr Tyr Lys Ser Glu Ser Ala Thr Phe Lys
             180                 185                 190

Cys Thr Ala Arg Gln Gly Ile Val Thr Arg Tyr Thr Gly Pro Phe Thr
         195                 200                 205

Thr Cys Pro Gln Ala Gly Val Leu Tyr Tyr Gly Gln Ser Val Thr Tyr
     210                 215                 220

Asp Thr Val Cys Lys Gln Asp Gly Tyr Val Trp Ile Ser Trp Thr Thr
225                 230                 235                 240

Asn Gly Gly Gln Asp Val Trp Met Pro Val Arg Thr Trp Asp Lys Asn
                 245                 250                 255

Thr Asp Ile Met Gly Gln Leu Trp Gly Asp Ile Tyr Leu Glu His His
             260                 265                 270

His His His His
         275

<210> SEQ ID NO 25
<211> LENGTH: 1050
<212> TYPE: DNA
<213> ORGANISM: Unknown
<220> FEATURE:
<223> OTHER INFORMATION: Phage or Bacteriophage  TWORT    PlyTW

<400> SEQUENCE: 25
atgaaaaccc tgaacaagc agagtcctac attaagagta agtaaatac aggaactgat      60 tttgatggtt tatatgggta tcagtgtatg gacttagcag tagattatat ttaccatgta    120
acagatggta aaataagaat gtggggtaat gctaaggatg cgataaataa ctcttttggt    180
ggtactgcta cggtatataa aaactacccct gcttttagac ctaagtacgg tgatgtagtc   240
gtatggacta ctggtaattt tgcaacttat ggtcatatcg caatagttac taaccctgac   300
ccttatggag accttcaata tgttacagtt cttgaacaaa actggaacgg taacgggatt   360
tataaaaccg agttagctac aatcagaaca cacgattaca caggaattac acattttatt   420
agacctaact ttgctactga atcaagtgta aaaaagaaag atacaaagaa aaaaccaaaa   480
ccatcaaata gagatggaat aaataaagat aaaattgtat atgatagaac taatattaat   540

```
tacaatatgg ttaaacgagg atataatcct gtaggtgtaa ttttacacaa cgatgctctc      600
gagactcagg ctgatataga aaacttaaa gaatatttta ttaaacaaat taaaatgtat       660
tatgaaggta aaacaccagt accaacagta gtaaatcaaa aagccaaaac aaaaccagtt      720
aagcagtcaa gtacaagtgg atggaacgtt aataattatg gtacttacta taaatccgag      780
agcgctacgt ttaagtgtac agcacgtcaa ggtatcgtta cacgatatac tggaccttt      840 actacgtgtc ctcaagcagg agtactatat tatggtcaat ctgtaactta tgatacggtt      900
tgtaagcaag atggttatgt atggattagt tggactacta atggaggtca agatgtttgg      960
atgcctgtaa gaacatggga taaaaacaca gacattatgg gtcagctatg gggagatata     1020
tatctcgagc accaccacca ccaccactga                                       1050
```

<210> SEQ ID NO 26
<211> LENGTH: 349
<212> TYPE: PRT
<213> ORGANISM: Unknown
<220> FEATURE:
<223> OTHER INFORMATION: Phage or Bacteriophage   TWORT    PlyTW

<400> SEQUENCE: 26

```
Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Asp Thr Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Leu Glu Thr Gln Ala Asp Ile Glu Lys
        195                 200                 205

Leu Lys Glu Tyr Phe Ile Lys Gln Ile Lys Met Tyr Tyr Glu Gly Lys
    210                 215                 220

Thr Pro Val Pro Thr Val Val Asn Gln Lys Ala Lys Thr Lys Pro Val
225                 230                 235                 240

Lys Gln Ser Ser Thr Ser Gly Trp Asn Val Asn Asn Tyr Gly Thr Tyr
                245                 250                 255

Tyr Lys Ser Glu Ser Ala Thr Phe Lys Cys Thr Ala Arg Gln Gly Ile
            260                 265                 270
```

```
Val Thr Arg Tyr Thr Gly Pro Phe Thr Thr Cys Pro Gln Ala Gly Val
        275                 280                 285

Leu Tyr Tyr Gly Gln Ser Val Thr Tyr Asp Thr Val Cys Lys Gln Asp
        290                 295                 300

Gly Tyr Val Trp Ile Ser Trp Thr Thr Asn Gly Gly Gln Asp Val Trp
305                 310                 315                 320

Met Pro Val Arg Thr Trp Asp Lys Asn Thr Asp Ile Met Gly Gln Leu
                325                 330                 335

Trp Gly Asp Ile Tyr Leu Glu His His His His His
                340                 345

<210> SEQ ID NO 27
<211> LENGTH: 70
<212> TYPE: DNA
<213> ORGANISM: Unknown
<220> FEATURE:
<223> OTHER INFORMATION: Primer

<400> SEQUENCE: 27
cgcgcgtcta gaaataattt tgtttaactt taagaaggag atatacatat gaaaaccctg    60
aaacaagcag                                                          70

<210> SEQ ID NO 28
<211> LENGTH: 30
<212> TYPE: DNA
<213> ORGANISM: Unknown
<220> FEATURE:
<223> OTHER INFORMATION: Primer

<400> SEQUENCE: 28
gtggtgctcg agatatatat ctccccatag                                    30

<210> SEQ ID NO 29
<211> LENGTH: 25
<212> TYPE: DNA
<213> ORGANISM: Unknown
<220> FEATURE:
<223> OTHER INFORMATION: Primer

<400> SEQUENCE: 29
ggagatatac atatgaaaac cctga                                         25

<210> SEQ ID NO 30
<211> LENGTH: 30
<212> TYPE: DNA
<213> ORGANISM: Unknown
<220> FEATURE:
<223> OTHER INFORMATION: Primer

<400> SEQUENCE: 30
acacctacct cgagatatcc tcgtttaacc                                    30

<210> SEQ ID NO 31
<211> LENGTH: 27
<212> TYPE: DNA
<213> ORGANISM: Unknown
<220> FEATURE:
<223> OTHER INFORMATION: Primer

<400> SEQUENCE: 31
ctgtaatcct gtcatctcga gagcatc                                       27
```

<210> SEQ ID NO 32
<211> LENGTH: 25
<212> TYPE: DNA
<213> ORGANISM: Unknown
<220> FEATURE:
<223> OTHER INFORMATION: Primer

<400> SEQUENCE: 32
ccactgattc tcgagatgcc aagct                                          25

<210> SEQ ID NO 33
<211> LENGTH: 28
<212> TYPE: DNA
<213> ORGANISM: Unknown
<220> FEATURE:
<223> OTHER INFORMATION: Primer

<400> SEQUENCE: 33
ctactaaaac tctcgagact caggctga                                       28

<210> SEQ ID NO 34
<211> LENGTH: 27
<212> TYPE: DNA
<213> ORGANISM: Unknown
<220> FEATURE:
<223> OTHER INFORMATION: Primer

<400> SEQUENCE: 34
ggtggtggtg ctcgagatat atatctc                                        27

<210> SEQ ID NO 35
<211> LENGTH: 23
<212> TYPE: DNA
<213> ORGANISM: Unknown
<220> FEATURE:
<223> OTHER INFORMATION: Primer

<400> SEQUENCE: 35
cgtagaggat cgagatctcg atc                                            23

<210> SEQ ID NO 36
<211> LENGTH: 26
<212> TYPE: DNA
<213> ORGANISM: Unknown
<220> FEATURE:
<223> OTHER INFORMATION: Primer

<400> SEQUENCE: 36
ccttgacgct cgagacactt aaacgc                                         26

<210> SEQ ID NO 37
<211> LENGTH: 69
<212> TYPE: DNA
<213> ORGANISM: Unknown
<220> FEATURE:
<223> OTHER INFORMATION: Primer

<400> SEQUENCE: 37 tccctctag aaataatttt gtttaacttt aagaaggaga tatacatatg agacctaact      60
ttgctactg                                                            69

<210> SEQ ID NO 38
<211> LENGTH: 32
<212> TYPE: DNA
<213> ORGANISM: Unknown
<220> FEATURE:

<223> OTHER INFORMATION: Primer

<400> SEQUENCE: 38
gcgatcgtcg actggaacgt taataattat gg                                32

<210> SEQ ID NO 39
<211> LENGTH: 38
<212> TYPE: DNA
<213> ORGANISM: Unknown
<220> FEATURE:
<223> OTHER INFORMATION: Primer

<400> SEQUENCE: 39
ctcgtcctcg agatatatat ctccccatag ctgaccca                          38

<210> SEQ ID NO 40
<211> LENGTH: 29
<212> TYPE: DNA
<213> ORGANISM: Unknown
<220> FEATURE:
<223> OTHER INFORMATION: Primer

<400> SEQUENCE: 40
cgcatactcg agagtagcaa agttaggtc                                    29

<210> SEQ ID NO 41
<211> LENGTH: 33
<212> TYPE: DNA
<213> ORGANISM: Unknown
<220> FEATURE:
<223> OTHER INFORMATION: Primer

<400> SEQUENCE: 41
cgcatactcg agaattttat ctttatttat tcc                               33

<210> SEQ ID NO 42
<211> LENGTH: 37
<212> TYPE: DNA
<213> ORGANISM: Unknown
<220> FEATURE:
<223> OTHER INFORMATION: Primer

<400> SEQUENCE: 42
cgcatactcg agagtagggt ctttacctac atgcaac                           37

<210> SEQ ID NO 43
<211> LENGTH: 29
<212> TYPE: DNA
<213> ORGANISM: Unknown
<220> FEATURE:
<223> OTHER INFORMATION: Primer

<400> SEQUENCE: 43
cgcatactcg agaacgttcc atccacttg                                    29

<210> SEQ ID NO 44
<211> LENGTH: 1512
<212> TYPE: DNA
<213> ORGANISM: Unknown
<220> FEATURE:
<223> OTHER INFORMATION: Phage or Bacteriophage  TWORT    PlyTW

<400> SEQUENCE: 44
atggctaaga ctcaagcaga aataaataaa cgtttagatg cttatgcaaa aggaacagta    60
gatagccctt acagagttaa aaaagctaca agttatgacc catcatttgg tgtaatggaa   120

```
gcaggagcca ttgatgcaga tggttactat cacgctcagt gtcaagacct tattacagac    180
tatgttttat ggttaacaga taataaagtt agaacttggg gtaatgctaa agaccaaatt    240
aaacagagtt atggtactgg atttaaaata catgaaaata aaccttctac tgtacctaaa    300
aaaggttgga ttgcggtatt tacatccggt agttatgaac agtggggtca cataggtatt    360
gtatatgatg gaggtaatac ttctacattt actattttag agcaaaactg gaatggttat    420
gctaataaaa aacctacaaa acgtgtagat aattattacg gattaactca cttcattgaa    480
atacctgtaa aagcaggaac tactgttaaa aaagaaacag ctaagaaaag cgcaagtaaa    540
acgcctgcac ctaaaaagaa agcaacacta aaagtttcta agaatcacat taactataca    600
atggataaac gtggtaaaaa acctgaagga atggtaatac acaacgatgc aggtcgttct    660
tcaggacaac aatacgagaa ttcattagct aatgcaggtt atgctagata cgctaatggt    720
attgctcatt actacggctc tgaaggttat gtatgggaag caatagatgc taagaatcaa    780
attgcttggc acacgggtga tggaacagga gcaaactcgg gtaactttag atttgcaggt    840
attgaagtct gtcaatcaat gagtgctagt gatgctcaat tccttaaaaa tgaacaagca    900
gtattccaat ttcagcagga gaatttaaa gaatggggtc ttactcctaa ccgtaaaact    960
gtaagattgc atatggaatt tgtaccaact gcctgtcctc accgttctat ggttcttcat   1020
acaggattta atccagtaac acaaggaaga ccatcacaag caataatgaa taaattaaaa   1080
gattatttca ttaaacaaat taaaaactac atggataaag gaacttcgag ttctacagta   1140
gttaaagatg gtaaaacaag tagcgcaagt acaccggcaa ctagaccagt tacaggttct   1200
tggaaaaaga accagtacgg aacttggtat aaaccggaaa atgcaacatt tgtcaatggt   1260
aaccaaccta gtaactag aataggttct ccattcttaa atgctccagt aggcggtaac   1320
ttaccggcag gggctacaat tgtatatgac gaagtttgta tccaagcagg tcacatttgg   1380
ataggttata atgcttacaa cggtaacaga gtatattgcc ctgttagaac ttgtcaaggt   1440
gttccaccta atcaaatacc tggcgttgcc tgggagtat tcaaactcga gcaccaccac   1500
caccaccact ga                                                       1512
```

<210> SEQ ID NO 45
<211> LENGTH: 503
<212> TYPE: PRT
<213> ORGANISM: Unknown
<220> FEATURE:
<223> OTHER INFORMATION: Phage or Bacteriophage TWORT PlyTW

<400> SEQUENCE: 45

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110
```

Glu Gln Trp Gly His Ile Gly Ile Val Tyr Asp Gly Asn Thr Ser
              115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
              180                 185                 190

Ser Lys Asn His Ile Asn Tyr Thr Met Asp Lys Arg Gly Lys Lys Pro
              195                 200                 205

Glu Gly Met Val Ile His Asn Asp Ala Gly Arg Ser Ser Gly Gln Gln
              210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
              260                 265                 270

Ser Gly Asn Phe Arg Phe Ala Gly Ile Glu Val Cys Gln Ser Met Ser
              275                 280                 285

Ala Ser Asp Ala Gln Phe Leu Lys Asn Glu Gln Ala Val Phe Gln Phe
              290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
              340                 345                 350

Gln Ala Ile Met Asn Lys Leu Lys Asp Tyr Phe Ile Lys Gln Ile Lys
              355                 360                 365

Asn Tyr Met Asp Lys Gly Thr Ser Ser Thr Val Lys Asp Gly
              370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
              405                 410                 415

Phe Val Asn Gly Asn Gln Pro Ile Val Thr Arg Ile Gly Ser Pro Phe
              420                 425                 430

Leu Asn Ala Pro Val Gly Gly Asn Leu Pro Ala Gly Ala Thr Ile Val
              435                 440                 445

Tyr Asp Glu Val Cys Ile Gln Ala Gly His Ile Trp Ile Gly Tyr Asn
450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys Leu
              485                 490                 495

Glu His His His His His His
              500

<210> SEQ ID NO 46
<211> LENGTH: 768

```
<212> TYPE: DNA
<213> ORGANISM: Unknown
<220> FEATURE:
<223> OTHER INFORMATION: Phage or Bacteriophage  TWORT     PlyTW

<400> SEQUENCE: 46
atggctgcaa cacatgaaca ttcagcacaa tggttgaata attacaaaaa aggatatggt      60
tacggcccct atccattagg tataaatggc ggtatgcact acggagttga ttttttatg      120 aatattggaa caccagtaaa agctatttca agcggaaaaa tagttgaagc tggttggagt      180
aattacggag gaggtaatca aataggtctt attgaaaatg atggagtgca tagacaatgg      240
tatatgcatc taagtaaata taatgttaaa gtaggagatt atgtcaaagc tggtcaaata      300
atcggttggt ctggaagcac tggttattct acagcaccac atttacactt ccaaagaatg      360
gttaattcat tttcaaattc aactgcccaa gatccaatgc ctttcttaaa gagcgcagga      420
tatggaaaag caggtggtac agtaactcca acgccgaata caggttggaa aacaaacaaa      480
tatggcacac tatataaatc agagtcagct agcttcacac ctaatacaga tataataaca      540
agaacgactg gtccatttag aagcatgccg cagtcaggag tcttaaaagc aggtcaaaca      600
attcattatg atgaagtgat gaaacaagac ggtcatgttt gggtaggtta tacaggtaac      660
agtggccaac gtatttactt gcctgtaaga acatggaata agtctactaa tactctgggt      720
gttctgtggg gaactataaa gctcgagcac caccaccacc accactga                  768

<210> SEQ ID NO 47
<211> LENGTH: 255
<212> TYPE: PRT
<213> ORGANISM: Unknown
<220> FEATURE:
<223> OTHER INFORMATION: Phage or Bacteriophage  TWORT     PlyTW

<400> SEQUENCE: 47

Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Lys Ala
    130                 135                 140

Gly Gly Thr Val Thr Pro Thr Pro Asn Thr Gly Trp Lys Thr Asn Lys
145                 150                 155                 160

Tyr Gly Thr Leu Tyr Lys Ser Glu Ser Ala Ser Phe Thr Pro Asn Thr
                165                 170                 175

Asp Ile Ile Thr Arg Thr Thr Gly Pro Phe Arg Ser Met Pro Gln Ser
            180                 185                 190
```

-continued

```
Gly Val Leu Lys Ala Gly Gln Thr Ile His Tyr Asp Glu Val Met Lys
        195             200             205

Gln Asp Gly His Val Trp Val Gly Tyr Thr Gly Asn Ser Gly Gln Arg
        210             215             220

Ile Tyr Leu Pro Val Arg Thr Trp Asn Lys Ser Thr Asn Thr Leu Gly
225             230             235             240

Val Leu Trp Gly Thr Ile Lys Leu Glu His His His His His His
                245             250             255
```

PHAGE TWORT ENDOLYSIN CHAP DOMAIN IS LYTIC FOR *STAPHYLOCOCCUS AUREUS*

BACKGROUND OF THE INVENTION

Field of the Invention

This invention relates to a nucleic acid sequence encoding a functional module or domain of a particular peptidoglycan hydrolase, i.e., the Phage Twort (PlyTW) endolysin, a protein which specifically attacks the cell wall peptidoglycan of untreated *Staphylococcus aureus*. The PlyTW endolysin is active over a broad range of physiological conditions including the pH and calcium concentration of bovine milk. The invention further relates to methods of treating diseases caused by the bacteria for which the PlyTW endolysin is specific.

Description of the Relevant Art

Global increases in antibiotic resistant pathogens have led to a renewed search for novel antimicrobials. One highly resistant bacterium, *Staphylococcus aureus*, has a high negative impact worldwide on the health of humans (Klevens et al. 2007. *JAMA* 298:1763-1771; WHO. 2014. In: *Antimicrobial Resistance: Global Report on Surveillance*, World Health Organization, Geneva, Switzerland), livestock (bovine, porcine, equine and poultry (Price et al. 2012. *M. Bio.* 3:e00305-e00311) and companion animals (dogs, cats, and horses) (Davis et al. 2014. *Lett. Appl. Microbiol.* 59:1-8; Harrison et al. 2014. *M. Bio.* 3:e00985-e0013). Recent estimates place *S. aureus* identified in hospitals at 70% resistant to methicillin, i.e., methicillin-resistant *S. aureus* (MRSA; Taubes, G. 2008. *Science* 321:356-361). Methicillin-resistant isolates, at lower frequencies, have been found in bovine mastitis isolates (Brody et al. 2008. *PLoS ONE* 3:e3074; Turutoglu et al. 2009. *Vet. Res. Commun.* 33:945-956; Alves et al. 2009. *Vet. Microbiol.* 137:190-195). Alternative antibiotic treatments, such as vancomycin in human infections, are rapidly losing efficacy as resistant strains are emerging, e.g., thirteen cases of vancomycin-resistant *S. aureus*, VRSA, have occurred in the United States since 2002 (CDC. 2013. In: *Antibiotic Resistance Threats in the United States* 2013. CDC, Atlanta). With increasing numbers of antibiotics proving to be ineffective, novel antibiotics are necessary to combat this emerging threat. Bacteriophage endolysins are a source of novel fusion antimicrobials that are uniquely poised to treat infections that are refractory to conventional antibiotic treatment (Donovan et al. 2009. *Biotech. International* 21:6-10).

Bacteriophage endolysins are peptidoglycan hydrolase enzymes encoded by bacteriophage (viruses that infect bacteria) to degrade the peptidoglycan component of the bacterial cell wall and thus allow nascent phage particles to escape the host cell (for review: Fischetti, V. A. 2008. *Curr. Opin. Microbiol.* 11:393-400; Donovan, D. M. 2007. *Recent Patents in BioTechnology* 1:113-122; Loessner, M. J. 2005. *Curr. Opin. Microbiol.* 8:480-487; Fischetti, V. A. 2010. *Int. J. Med. Microbiol.* 300:357-4362; Nelson et al. 2012. *Adv. Virus Res.* 83:299-365; Shen et al. 2012. In: *Bacteriophages in Health and Disease*, Hyman and Abedon, Eds., CABI, Wallingford, UK, pp. 217-239.) Endolysins can harbor any of three unique activities: endopeptidase, amidase (Becker et al. 2009a. *FEMS Microbiol. Lett.* 294:52-60 Navarre et al. 1999. *J. Biol. Chem.* 274:15847-15856) or glycosidase activity (Pritchard et al. 2007. *Appl. Environ. Microbiol.* 73:7150-7154) (for review see Loessner, M. J. 2005, supra). The exact amino acid sequence and composition of the Gram positive peptidoglycan can vary between genera or even between species within a genus (Schleifer and Kandler. 1972. *Bacteriol. Rev.* 36:407-477). The near-species specificity of the Gram positive peptidoglycan structure and the specificity of the endolysin domains distinguish these enzymes as potential narrow spectrum antimicrobials.

Thus, because of the rise of drug resistant pathogenic bacteria, there is a need for new pathogen-specific antimicrobial treatments. Reagents that are specific for the genera, species or strains of concern and that are also refractory to resistance development are important for effective control of disease and therapeutic treatments.

SUMMARY OF THE INVENTION

We have discovered that the nucleic acid encoding the Phage Twort (PlyTW) endolysin, a protein which specifically attacks the peptidoglycan cell wall of untreated *S. aureus* can be truncated and that PlyTW phage endolysin, and also truncations of PlyTW prophage endolysin, can be used as an antimicrobial treatment for mastitis as well as for infection and for other human diseases, such as infection and disease caused by multidrug-resistant staphylococci.

In accordance with this discovery, it is an object of the invention to provide nucleic acid molecules encoding PlyTW endolysin or truncated PlyTW endolysin polypeptides.

It is also an object of the invention to provide an antimicrobial PlyTW endolysin or a truncated PlyTW endolysin, which is functional, i.e., retains its properties for degrading the peptidoglycan cell wall of the Gram-positive bacteria.

An added object of the invention is to provide a nucleic acid sequence encoding PlyTW endolysin or truncated PlyTW endolysin polypeptides according to the invention as an encoding sequence which allows disease resistance to be imparted to the organism. It is well understood that this sequence can also be used in combination with another sequence, or sequences, encoding one or more disease resistant properties.

It is an object of the invention to provide a nucleic acid sequence encoding PlyTW endolysin or truncated PlyTW endolysin polypeptides according to the invention as an encoding sequence which can be expressed in the mammary glands of transgenic cattle.

It is a further object of the invention to provide a fusion nucleic acid encoding an antimicrobial fusion protein formed from a nucleic acid encoding a functional module or domain of the PlyTW endolysin, a protein which specifically attacks the peptidoglycan cell wall of untreated *S. aureus* in combination with nucleic acid encoding a functional module(s) or domain(s) of another endolysin(s) having a different hydrolase activity, e.g., glycosidase, amidase and endopeptidase activity.

A still further object of the invention also relates to a chimeric gene (or expression cassette) comprising an encoding sequence as well as heterologous regulatory elements in positions 5' and 3' which can function in a host organism, the encoding sequence comprising at least one nucleic acid sequence encoding an antimicrobial PlyTW endolysin or a truncated PlyTW endolysin.

An additional object of the invention is to provide a host organism into which the PlyTW gene, or truncated gene, according to the invention can be introduced so as to produce an endolysin or truncated endolysin.

An added object of the invention is to provide pharmaceutical compositions comprising an antimicrobial PlyTW endolysin or a truncated PlyTW endolysin, comprising the CHAP domain alone or the CHAP domain and the cell wall binding domain, compositions useful for the treatment of disease.

A further object of the invention is to provide compositions useful for the treatment of diseases and infections caused by the bacteria for which the PlyTW endolysin and truncated PlyTW endolysin are specific, where the composition comprises the PlyTW endolysin, the CHAP domain PlyTW 146', or PlyTWΔ146-373 and PlyTWΔ172-373, each comprising the CHAP domain and the SH3b cell wall binding domain.

Another object of the invention is to provide a method of treating diseases and infections with the polypeptides of the invention, PlyTW endolysin, PlyTW 146', PlyTWΔ146-373 or PlyTWΔ172-373, wherein said diseases and infections are caused by the bacteria for which these polypeptides are specific.

Also part of this invention is a kit, comprising a composition for treatment of disease caused by the bacteria for which the PlyTW endolysin and truncated PlyTW endolysin are specific.

Other objects and advantages of this invention will become readily apparent from the ensuing description.

BRIEF DESCRIPTION OF THE DRAWINGS

FIG. 1A depicts a schematic representation of the full length PlyTW endolysin (SEQ ID NO:2), LysK (SEQ ID NO: 45), Lysostaphin (SEQ ID NO:47) and PlyTW deletion constructs with domains labeled as identified in the Pfam domain database: (retrieved from the Internet:<URL: pfam.sanger.ac.uk/protein?entry=056788). Fusion junction points are noted: Endopeptidase domain (solid grey), CHAP domain (diagonal stripes), amidase domain (vertical stripes), SH3b domain (horizontal stripes), 6×His tag (black box). At each fusion junction, and 6×His tag, there is an XhoI restriction enzyme site introduced (corresponding to an LE sequence in the amino acid sequence). Endolysin sequences and SH3b sequences are drawn to scale. His tags are not drawn to scale. The proteins PlyTW 146', PlyTW 172', PlyTW 188', PlyTW 199', PlyTW 245', PlyTW 323', PlyTW 376', PlyTW 392', PlyTW '141-392, PlyTW Δ146-373, PlyTW Δ172-373, and PlyTW Δ199-325 are identified by SEQ ID NOs: 4, 6, 8, 10, 12, 14, 16, 18, 20, 22, 24 and 26, respectively; FIG. 1B and FIG. 1C show the SDS-PAGE analysis and Zymogram analysis, respectively, of 1 μg nickel column-purified proteins corresponding to the constructs in FIG. 1A. FIG. 1D shows the Turbidity Reduction analysis of the expressed proteins. Specific activities (ΔOD$_{600\ nm}$/μm/min) for the PlyTW constructs are presented as the maximal change in OD$_{600\ nm}$ (during a 40 sec interval at three time points) over the 30 minute assay. Each data point (+/−SD) represents samples at 0.5 μM protein, in 150 mM NaCl SLB from at least two experiments performed in triplicate (n≥6).

FIG. 3A shows the addition of PlyTW (black diamonds), PlyTW 146' (white squares), PlyTW Δ146-373 (white triangles) and PlyTW Δ172-373 (black triangles) to the turbidity reduction assay to a final concentration of 5 μM in 150 mM SLB, and at 2 fold serial dilutions. The OD$_{600\ nm}$ was measured in triplicate every 20 sec for 10 minutes. Activities are reported as maximal ΔOD$_{600\ nm}$/min) (+/−SD). Due to the different levels of activity, the data are represented with two y axes: black markers correspond to the left axis, white markers correspond to the right axis. FIG. 3B shows PlyTW constructs assayed at 1 μm concentrations in SLB with NaCl concentrations of 67.5, 100, 150, 200, 300, 400 and 500 mM. Specific activities (maximal ΔOD$_{600\ nm}$/μm/min) for the PlyTW constructs are presented. Each data point (+/−SD) represents triplicate samples at 1 μM from at least two experiments performed in triplicate (n≥6).

DETAILED DESCRIPTION OF THE INVENTION

Figures 1A, 1B, 1C, 1D:
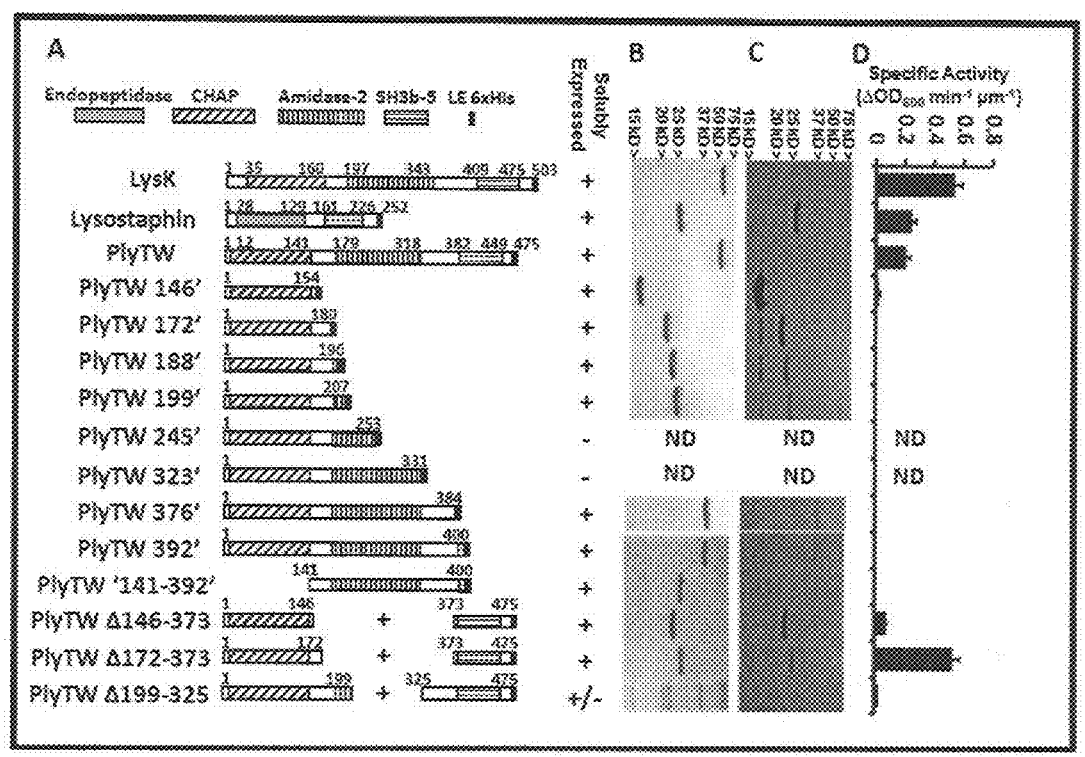
FIGS. 1A-1D depict schematic representations and SDS-PAGE, Zymogram and Turbidity Reduction analyses of PlyTW constructs.

The *Staphylococcus aureus* bacteriophage Twort endolysin (PlyTW) is a multi-domain endolysin, 467 amino acids (aa) in length, and according to the PFAM domain data base: (retrieved from the Internet: <URL: pfam.sanger.ac.uk/protein?entry=056788) (Finn et al. 2008. *Nucleic Acids Res.* 36:D281-D288), contains a cysteine, histidine dependent amidohydrolase/peptidase (CHAP endopeptidase) domain (12-141 aa), an amidase-2 domain (179-318aa) and a SH3b-5 cell wall binding domain (CBD: 382-449aa). The PlyTW endolysin gene was first isolated and its activity described in 1998 by Loessner et al. (1998. *FEMS Microbiol. Lett.* 162:265-274). A truncated version of PlyTW harboring the CHAP domain and a truncated amidase domain was shown to have an N-acetyl-muramoyl-L-alanine amidase activity (Loessner et al. 1998, supra). Truncations of PlyTW and the Twort phage holin protein, HolTW were over-expressed in *E. coli* and shown to be sufficient to lyse *S. aureus* cells (Loessner et al. 1998, supra). Additionally, Daniel et al. (2010. *Antimicrob. Agents Chemother.* 54:1603-1612) and Pastagia et al. (2011. *Antimicrob. Agents Chemother.* 55:738-744) have described fusions with the PlyTW N-terminal CHAP domain fused to the cell wall binding domain of phiNM3 endolysin, demonstrating its effectiveness as an antimicrobial. This work expands on earlier studies by presenting a more complete deletion analysis of PlyTW, to determine the contribution of each domain to the lytic activity individually and in combination with the other domains.

The Twort phage endolysin shares a common domain architecture (CHAP-amidase-SH3b) with numerous SH3b-containing staphylolytic phage endolysins. The SH3b-containing staphylolytic phage endolysins collated from public data sets with this domain architecture have been catalogued into three conserved groups based on amino acid identity (97% within group amino acid identity; less than 50% between group amino acid identity) (Becker et al. 2009b. *Gene* 443:32-41). PlyTW is highly divergent from these three groups sharing only 57% identity to its most conserved homologue, PhiWMY endolysin (Becker et al. 2009b, supra; Yokoi et al. 2005. *Gene* 351:97-108). The unique sequences of PlyTW suggesting altered "functional specificity" compared to other SH3b-containing endolysins, making it a potential novel antimicrobial. This work demonstrates that the CHAP domain of PlyTW is necessary and sufficient for exolysis of *S. aureus* cells in three lytic assays. The SH3b domain enhances the activity of the CHAP domain, but is not essential for CHAP lytic activity. CHAP domains that are essential for cell lysis have been identified previously for two staphylococcal endolysins that share a domain organization nearly identical to the Twort endolysin, namely: LysK (Becker et al. 2009a, supra; Horgan et al. 2009. *Appl. Environ. Microbiol.* 75:872-874, and the phi11 endolysin (Donovan et al. 2006. *FEMS Microbiol. Lett.* 265:133-139; Sass and Bierbaum. 2007. *Appl. Environ. Microbiol.* 73:347-352).

The N-terminal CHAP domain of PlyTW construct 146' (SEQ ID NO:3) was active in each of the three lytic assays, suggesting that the N-terminus of the protein plays an essential role in cell lysis. These findings are supported by a previous study where Loessner et al. (1998, supra) first isolated the PlyTW gene from the Twort phage genome and identified three phage genomic clones that each expressed a different form of PlyTW in *E. coli*. The full length 467 aa and two C-terminal truncations (1-271 aa and 1-172 aa) were expressed from phage genomic clones, and these researchers arrived at the same conclusion as we have, namely that the N-terminal region of the protein contains the primary active domain. Interestingly, this early study described an increase of free alanine amino groups (detected as dinitrophenyl (DNP)-labeled alanine by RP-HPLC) after digestion of *S. aureus* cell walls with the longest truncation (1-271 aa) indicating an amidase activity. However, in our assays, the amidase domain alone (PlyTW 141-392) showed no lytic activity in any assay (data not shown). These negative results raise concerns about any truncation where there is potential for non-native constructs to lack activity due to improper folding.

The heightened activity levels of the amidase deletion construct PlyTW Δ172-373 is in contrast to the findings with the staphylococcal phage K endolysin, LysK, where deletion of the amidase domain had minimal effect on the exolytic activity of the truncated protein (Becker et al. 2009a, supra). This may be explained simply due to the non-native structure of these constructs, in so far as two additional internal deletion constructs were generated and tested in parallel with each showing reduced activity compared to the full length protein (FIG. 1D). Similar to our construct PlyTW Δ172-373, the N-terminal domain (within the 184 aa PlyTW fragment) has been incorporated into a fusion (ClyS) by the Fischetti Laboratory fusing the CHAP domain of PlyTW to the phiNM3 phage endolysin's cell wall binding domain (Daniel et al., supra).

Consistent with the LysK deletions and fusions (Becker et al. 2009, supra) and the ClyS fusion (Daniel et al., supra), when the PlyTW CHAP domain is fused to a cell wall binding domain, the CHAP domain turbidity reduction assay activity increased approximately 10 fold (Becker et al. 2009, supra). This is also similar to the work of Sass and Bierbaum (supra) with the phi11 endolysin where the CHAP domain alone was active, but the CHAP-SH3b fusion was much more active on both purified staphylococci cell walls and SDS-treated cells. The PlyTW SH3b domain was fused to the Ply TW CHAP domain in three different constructs (PlyTW Δ146-373, PlyTW Δ172-373, PlyTW Δ199-325; SEQ ID NOs: 21, 23 and 25, respectively). The PlyTW Δ199-325 construct purified poorly and thus showed little to no improved turbidity reduction activity. However, the PlyTW Δ146-373 activity increased the activity of the CHAP domain by approximately 4 fold and the construct PlyTW Δ172-373 increased the turbidity reduction activity exceeding the activity of the full length PlyTW activity levels by approximately 2 fold, approaching the LysK activity levels (FIG. 1D). Similarly, deletion of the SH3b domain from the full length construct (Ply TW 392) reduced the turbidity reduction activity of the full length Ply TW construct to virtually undetectable levels, although at high enough concentrations, activity was detectable in both the plate lysis and turbidity reduction assays (data not shown). This dependence on C-terminal cell wall binding domain sequences for full lytic activity has been demonstrated previously, for the staphylococcal proteins LysK (Becker et al. 2009a, supra), phi11/LytA endolysin (Donovan et al. 2006, supra; Sass and Bierbaum, supra), Lysostaphin (Baba and Schneewind. 1996. *EMBO J.* 15:4789-4797, ALE-1 (Lu et al. 2006. *J. Biol. Chem.* 281:549-558), and the Listeria phage proteins Ply118 and Ply500 (Loessner et al. 2002. *Mol. Microbiol.* 44:335-349). However, there may be other factors at work because the opposite effect has been observed for the streptococcal B30 endolysin (Donovan et al. 2006, supra), its nearly identical homologue PlyGBS (Cheng and Fischetti. 2007. *Appl. Microbiol. Biotechnol.* 74:1284-1291), as well as the *bacillus* endolysin Ply L (Low et al. 2005. *J. Biol. Chem.* 280:35433-35439), where a truncated protein (lacking a cell wall binding domain) shows higher activity in the absence of the C-terminal cell wall binding domain. Even more confounding is the work of Hogan et al. which reported that the first 165 amino acids of LysK (CHAP domain) alone, lacking an SH3b cell wall binding domain, expressed a lytic activity that was even greater than full length LysK (Horgan et al., supra). These discrepancies in reported dependence on cell wall binding domains may reflect the vagaries of the unique assay conditions (e.g., buffer constituents) employed by different labs to perform peptidoglycan hydrolase activity measurements, for example, in FIG. 3b, the PlyTW 146' construct lacking a cell wall binding domain has greater activity in turbidity reduction assays than the full length protein at reduced salt concentrations (50 mM and 100 mM NaCl).

The differences in activity levels of the many staphylococcal phage endolysin deletion and fusion constructs apparent in the literature demonstrate the need for empirical testing of each novel construct. There is also an indication from numerous labs that the differences in quantitative results of the same construct in different peptidoglycan hydrolase assays (e.g., plate lysis vs. turbidity reduction vs. zymogram) that there is still a gap in our understanding as to exactly what each assay is measuring. However, these discrepancies and the lack of uniformity of assay conditions between labs, has the added benefit of supporting the argument that these enzymes can likely be tailored to very specific and unique therapeutic applications. For example, the PlyTW Δ172-373 and PlyTW 146' constructs show much higher activity than full length PlyTW or other CHAP domain constructs in the presence of elevated $Ca^{2+}$, suggesting that these constructs might be strong candidates for treating bovine mastitis, where the calcium concentration in milk is about 30 mM. With continued analysis, there will likely be other unique and unexpected properties of these novel antimicrobials that will lend themselves to very specific and unexpected therapeutic or preventative applications.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the PlyTW endolysin according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional PlyTW endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of PlyTW endolysin" refers to all fragments of PlyTW endolysin that retain PlyTW endolysin activity and function to lyse staphylococcal bacteria.

Modifications of the PlyTW endolysin primary amino acid sequence may result in further mutant or variant proteins having substantially equivalent activity to the PlyTW endolysin polypeptides described herein. Such modifications may be deliberate, as by site-directed mutagenesis, or may occur by spontaneous changes in amino acid sequences where these changes produce modified polypeptides having substantially equivalent activity to the PlyTW endolysin polypeptide. Any polypeptides produced by minor modifications of the PlyTW endolysin primary amino acid sequence are included herein as long as the biological activity of PlyTW endolysin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a PlyTW endolysin polypeptide and which hybridize under stringent conditions to the PlyTW endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have PlyTW endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the PlyTW endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, PlyTW endolysin activity as described herein. Such variants may result from, for example, genetic polymorphism or from human manipulation. Biologically active variants of a native PlyTW endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired PlyTW endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of PlyTW endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat. or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmids, Constructs and Strains

The Twort genomic DNA clone was kindly provided by Martin Loessner (Lossener et al. 1998, supra) with the protein sequence available through Genbank (CAA69021.1). Truncations of PlyTW were produced using standard PCR cloning methods as described previously for the full length PlyTW plasmid p5719 (Becker et al. 2009a, supra); FIG. 1A. Sequences were PCR amplified using primers indicated in Table 1. Amplified fragments were subsequently purified, digested with XbaI and XhoI and subcloned into pET21a (EMD Biosciences, San Diego, Calif.), using standard techniques. All pET21a-derived constructs (Table 2) have an additional eight amino acids at the C-terminus composed of LE (XhoI restriction enzyme cloning site), and a 6×His tag for nickel chromatography purification. Plasmids PlyTW Δ146-373 and PlyTW Δ172-373, do not have LE (XhoI restriction enzyme cloning site), but rather have LD as the additional two amino acids introduced by the ligation of XhoI-SalI cut sites at the fusion junction. Construct PlyTW Δ199-325 was generated with an internal XhoI site, generating two additional amino acids (LE) at the fusion junction. All subcloning was performed in *E. coli* DH5α (Invitrogen, Carlsbad, Calif.) and construct accuracy verified by DNA sequence analysis. Constructs cloned into pET21a were expressed in *E. coli* BL21 (DE3) (EMD Biosciences, San Diego, Calif.) for protein purification.

*S. aureus* Newman strain was grown at 37° C. in either tryptic soy broth (TSB) (Becton Dickenson, Sparks, Md.) for plate lysis assays or Brain Heart Infusion (BHI) broth (BD, Sparks, Md.) for both turbidity reduction assays and zymogram analysis.

TABLE I

Primers

| # | Primer | Sequence | SEQ ID NO: |
|---|--------|----------|------------|
| 1 | TWXBA-F | 5'-CGCGCG<u>TCTAGA</u>AATAATTTTGTTTAACTTTAAGAAG GAGATATA<u>CATATG</u>AAAACCCTGAAACAAGCAG-3' | 27 |
| 2 | TWXHOI-R | 5'-GTGGTG<u>CTCGAG</u>ATATATATCTCCCCATAG-3' | 28 |
| 3 | TWNDEI-F | 5'-GGAGATATA<u>CATATG</u>AAAACCCTGA-3' | 29 |
| 4 | TWXHOI-188R | 5'-ACACCTAC<u>CTCGAG</u>ATATCCTCGTTTAACC-3' | 30 |

TABLE I-continued

Primers

| # | Primer | Sequence | SEQ ID NO: |
|---|---|---|---|
| 5 | TWXHOI-199R | 5'-CTGTAATCCTGTCATCTCGAGAGCATC-3' | 31 |
| 6 | TWXHOI-245R | 5'-CCA CTG ATT CTC GAG ATG CCA AGC T-3' | 32 |
| 7 | TWXHOI-325F | 5'-CTACTAAAACTCTCGAGACTCAGGCTGA-3' | 33 |
| 8 | TWXHOI-467R | 5'-GGTGGTGGTGCTCGAGATATATATCTC-3' | 34 |
| 9 | TWBGLIIF | 5'-CGTAGAGGATCGAGATCTCGATCC-3' | 35 |
| 10 | TWXHOI-392R | 5'-CCTTGACGCTCGAGACACTTAAACG C-3' | 36 |
| 11 | TWXBAI-141F | 5'-TCCCCTCTAGAAATAATTTTGTTTAACTTTAAGAAGG AGATATACATATGAGACCTAACTTTGCTACTG-3' | 37 |
| 12 | TWSALI-373F | 5' GCGATCGTCGACTGGAACGTTAATAATTATGG-3' | 38 |
| 13 | TWXHOI-475R | 5' CTCGTCCTCGAGATATATATCTCCCCATAGCTGACCCA-3' | 39 |
| 14 | TWXHOI-146R | 5' CGCATACTCGAGAGTAGCAAAGTTAGGTC-3' | 40 |
| 15 | TWXHOI-172R | 5' CGCATACTCGAGAATTTTATCTTTATTTATTCC-3' | 41 |
| 16 | TWXH01-323R | 5' CGCATACTCGAGAGTAGGGTCTTTACCTACATGCAAC-3' | 42 |
| 17 | TWXH01-376R | 5' CGCATACTCGAGAACGTTCCATCCACTTG-3' | 43 |

TABLE 2

Constructs and Primers

| Construct | Primer 1 # | Primer 2 # | Cloning Vector | SEQ ID NO: Nucleic Acid | SEQ ID NO: Protein |
|---|---|---|---|---|---|
| PlyTW (5719) | 1 | 2 | pET21a | 1 | 2 |
| PlyTW 146' | 1 | 14 | pET21a | 3 | 4 |
| PlyTW 172' | 1 | 15 | pET21a | 5 | 6 |
| PlyTW188 | 3 | 4 | pET21a | 7 | 8 |
| PlyTW 199' | 3 | 5 | pET21a | 9 | 10 |
| PlyTW 245' | 1 | 6 | pET21a | 11 | 12 |
| PlyTW 323' | 1 | 16 | pET21a | 13 | 14 |
| PlyTW 376' | 1 | 17 | pET21a | 15 | 16 |
| plyTW 392 | 9 | 10 | pET21a | 17 | 18 |
| plyTW 141-392 | 11 | 10 | pET21a | 19 | 20 |
| PlyTW Δ146-373 | 12 | 13 | PlyTW 146' | 21 | 22 |
| PlyTW Δ172-373 | 12 | 13 | PlyTW 172' | 23 | 24 |
| PlyTW Δ199-328 | 7 | 8 | PlyTW199 | 25 | 26 |

The primer # refers to the sequences of Table 1.

Example 2

Protein Expression, Purification and Analysis

Purification of recombinant peptidoglycan hydrolase constructs for in vitro assays was performed per manufacturer's instructions (Qiagen, Ni-NTA, Germantown, Md.) with the following modifications. Protein inductions were performed in modified LB (tryptone, 15 g/liter; yeast extract, 8 g/liter; NaCl, 5 g/liter; pH 7.8) (Schmelcher et al. 2010. *Appl. Environ. Microbiol.* 76:5745-5756) at 10° C. for 20 h. To avoid solubility issues, 30% glycerol was included in all purification buffers. All samples were filter sterilized through a 0.22-micron after elution and protein concentrations were determined via a nanodrop spectrophotometer (Thermo Fisher Scientific, Waltham, Mass.). Sterilized protein preparations were stored at 4° C. until time of assay, and the purity of each preparation was determined by SDS-PAGE analysis.

The 467 codon gene plyTW was subcloned into the pET21a vector, which adds six histidine codons at the C-terminus. This construct (FIG. 1A; PlyTW) retained all three protein domains, CHAP endopeptidase, amidase-2, and the SH3b cell wall binding domain. Truncations and deletions of the PlyTW gene were generated by PCR-subcloning (Becker et al. 2009a, supra) (FIG. 1A) to determine the activities of each domain individually or in combination. The addition of a 6×His tag facilitated protein purification via nickel column chromatography.

One μg of the purified fusion proteins and Kaleidoscope protein standards (Invitrogen) were analyzed by 15% SDS-PAGE in Tris-Glycine buffer at 100 v for 1.5 h in the BioRad Mini-PROTEAN 3 gel apparatus (BioRad, Hercules, Calif.) according to the manufacturer's instructions. Zymogram gels were prepared with 300 ml equivalent of mid-logarithmic phase ($OD_{600\ nm}$ of 0.4-0.6) *S. aureus* Newman cells embedded in the gels and electrophoresed simultaneously with the SDS-PAGE gels. The SDS-PAGE gels were stained with Coomassie blue using standard protocols as described previously (Becker et al. 2009a, supra). Zymograms were washed twice in excess water for 30 min to remove SDS and incubated for <1 h at room temperature in water until cleared zones developed.

The SDS-PAGE analysis (FIG. 1B) indicates that each construct was expressed in *E. coli* and most purified to greater than 95% purity via nickel column chromatography (except constructs PlyTW245', PlyTW 323', and PlyTWΔ199-325). Zymogram analysis indicated that the predicted protein in most preparations was the only active protein species (LysK and Lysostaphin, PlyTW 146', PlyTWΔ146-373 and PlyTWΔ172-373). These constructs indicate that the CHAP domain alone is sufficient to clear a spot in the zymogram gel while the amidase domain alone (PlyTW142-392) is not. [The SH3b cell wall binding domain is not expected to have any lytic activity and was not tested independently.] Interestingly, a shadow band (potentially representing a truncated CHAP domain band) approximately the size of the CHAP domain alone (PlyTW 146') is consistently observed in the zymogram for constructs PlyTW, PlyTW 172', PlyTW 188', PlyTW 199', PlyTW 376', and PlyTW 392' (FIG. 1C) while no corresponding band is apparent in the parallel SDS gel. In an attempt to enhance the CHAP domain activity, fusions of the CHAP domain to the Sh3B domain were constructed (PlyTWΔ146-373 and PlyTWΔ172-373). Previous studies demonstrated that a deletion of the amidase domain from a similarly structured lysin, LysK, resulted in no loss of activity as compared to the full length protein (Becker et al. 2009, supra). These constructs did show activity in the zymogram, but the activity was not enhanced over the shortest CHAP domain alone construct (PlyTW 146').

Example 4

Turbidity Reduction Assay

To further quantify the PlyTW lytic activity against live *S. aureus* each purified protein was tested in turbidity reduction assays. The turbidity assay was modified from the plate reader assay reported previously (Becker et al. 2009a, supra). Enzymes were serially diluted in SLB in wells of a 96 well plate, and reactions were initiated with the addition of thawed *S. aureus* substrate cells (Becker et al. 2009b, supra) (mid-log phase grown cells, frozen in SLB supplemented with 30% glycerol, thawed, washed 3× in excess SLB) resuspended in SLB supplemented with varying concentrations of lytic protein, NaCl, CaCl$_2$, MgCl$_2$, MnSO$_4$, ZnSO$_4$ or EDTA at room temperature. Enzymes were equilibrated in the appropriate buffer for 10 min prior to the initiation of each reaction. The maximum rate for each reaction (calculated as a sliding window of 40 seconds as determined by a plate reader with OD$_{600\ nm}$ readings taken every 20 sec) was reported as turbidity reduction rate (ΔOD$_{600\ nm}$/min) or divided by the μM concentration of each protein in the sample to yield a specific activity (ΔOD$_{600\ nm}$/μM/min).

The previously characterized LysK phage endolysin (Becker et al., supra; O'Flaherty et al. 2005. *J. Bacteriol.* 187:7161-7164; Becker et al. 2009a, supra) and the endopeptidase Lysostaphin (Browder et al. 1965. *Biochem. Biophys. Res. Commun.* 19:389) were positive control enzymes. When tested in parallel (FIG. 1D) at a concentration of 0.5 μM in 150 mM SLB, the activity (ΔOD$_{600\ nm}$/μm/min) of LysK (0.54+/−0.05) was at least 2.2 fold greater than either lysostaphin (0.25+/−0.02) or wt PlyTW (0.21+/−0.02). Deletions, eliminating the SH3b cell wall binding domain, reduced the activity in the turbidity reduction assay, minimally 8.6 fold (PlyTW vs. PlyTW 146' [0.024+/−0.006]). Internal deletions of the amidase domain, and the surrounding undefined regions, have varied effects. PlyTWΔ146-373 (0.079+/−0.003) increased activity 3.3 fold compared to the CHAP domain alone. A second internal deletion, PlyTWΔ172-373, exceeded PlyTW activity, and achieved nearly the same activity as LysK, (0.53+/−0.04). An additional internal deletion, PlyTWΔ199-325, eliminated the ability to readily purify the construct over background proteins (FIG. 1B). The remaining deletion constructs, while active in the zymogram assay, show no detectable activity at 0.5 μM in the turbidity reduction assay. It is not uncommon for peptidoglycan hydrolase enzymes to give quantitatively different results in a variety of peptidoglycan hydrolase assays, as has been reported for Lysostaphin (Kusuma and Kokai-Kun. 2005. *Antimicrob. Agents Chemother.* 49:3256-3263).

Figures 3A, 3B:
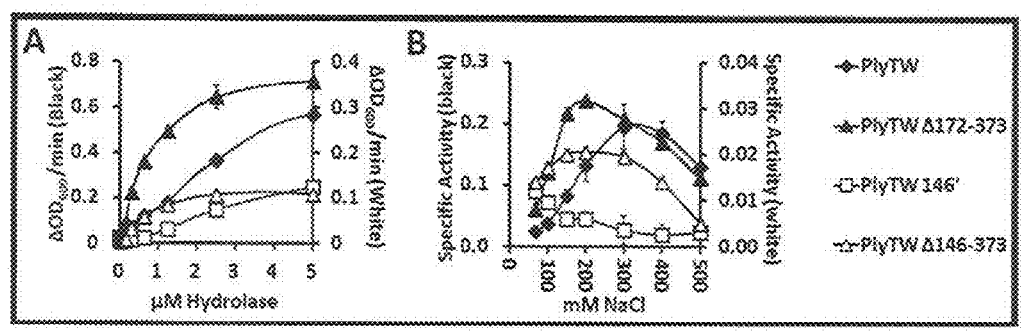
FIGS. 3A and 3B depict the effect of hydrolase and salt concentration of the PlyTW constructs in the Turbidity Reduction Assay.

The effects of enzyme concentration and salt concentration were evaluated. Each of the four constructs was tested at increasing enzyme concentrations to determine the linear range and appropriate molar concentration for further comparisons (FIG. 3A). The lowest equimolar concentration where all four constructs are reliably active was determined to be between 0.6-1.3 μM. Comparative turbidity reduction assays were performed at 1 μM. When each of the enzymes were tested over a range of NaCl concentrations, PlyTW had maximum activity at 300 mM NaCl, whereas both internal deletions of the amidase domain (PlyTWΔ146-373 and PlyTWΔ172-373) had optimal activity at 200 mM NaCl, closer to physiological saline concentrations. PlyTW 146' had maximal activity at 67.5 mM NaCl, the lowest concentration tested (FIG. 3B).

Figures 4A, 4B, 4C, 4D:
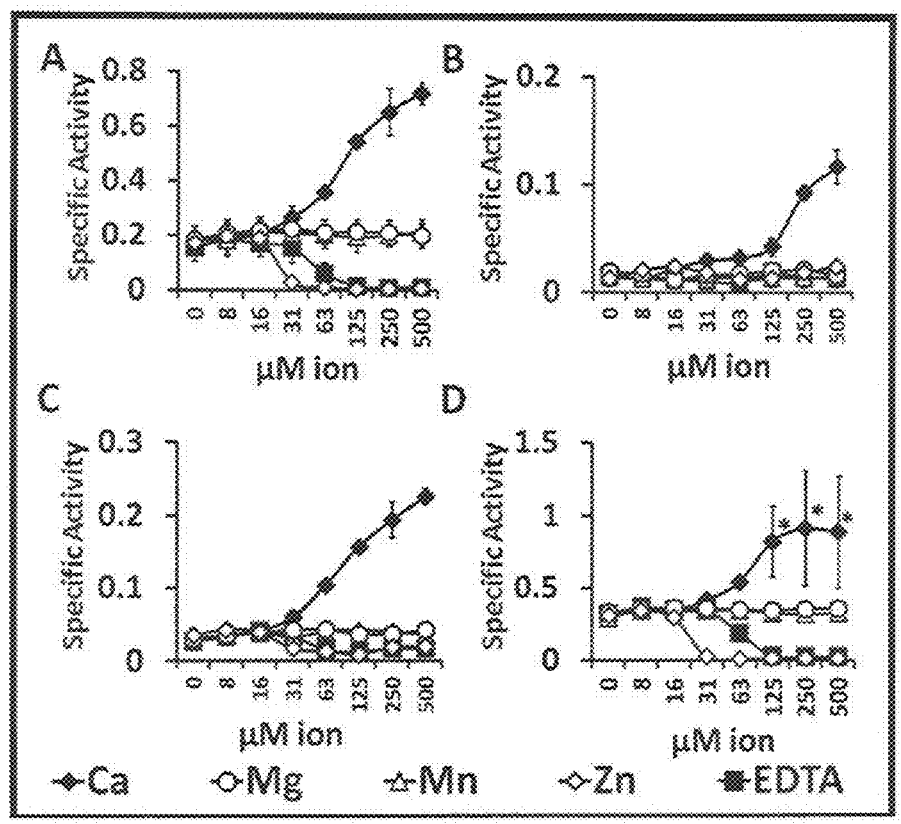
FIGS. 4A-4D depict the effect of divalent cations on PlyTW construct activity on staphylococcal strain Newman cells in Turbidity Reduction Assays. Live *S. aureus* were resuspended in SLB (20 mM Tris, pH 7.5, 150 mM NaCl) supplemented with 2 fold serial dilutions of each ion, or EDTA, from 0.5 mM. PlyTW (FIG. 4A), PlyTW 146' (FIG. 4B), PlyTW Δ146-373 (FIG. 4C) and PlyTW Δ172-373 (FIG. 4D), each at 1 μM concentration, were tested over gradients of $Ca^{2+}$ (black diamonds), $Mg^{2+}$ (white circles), $Mn^{2+}$ (white triangles), $Zn^{2+}$ (white diamonds), or EDTA (black squares). The OD$_{600\ nm}$ was measured in triplicate every 20 sec for 10 minutes. Each specific activity (+/−SD) represents samples performed in at least triplicate (n≥3). Asterisks indicated samples which significantly cleared the assay before the initial time point thus increasing the variability of the assay, and under represent the activity of the hydrolase under these conditions.
Figure 5:
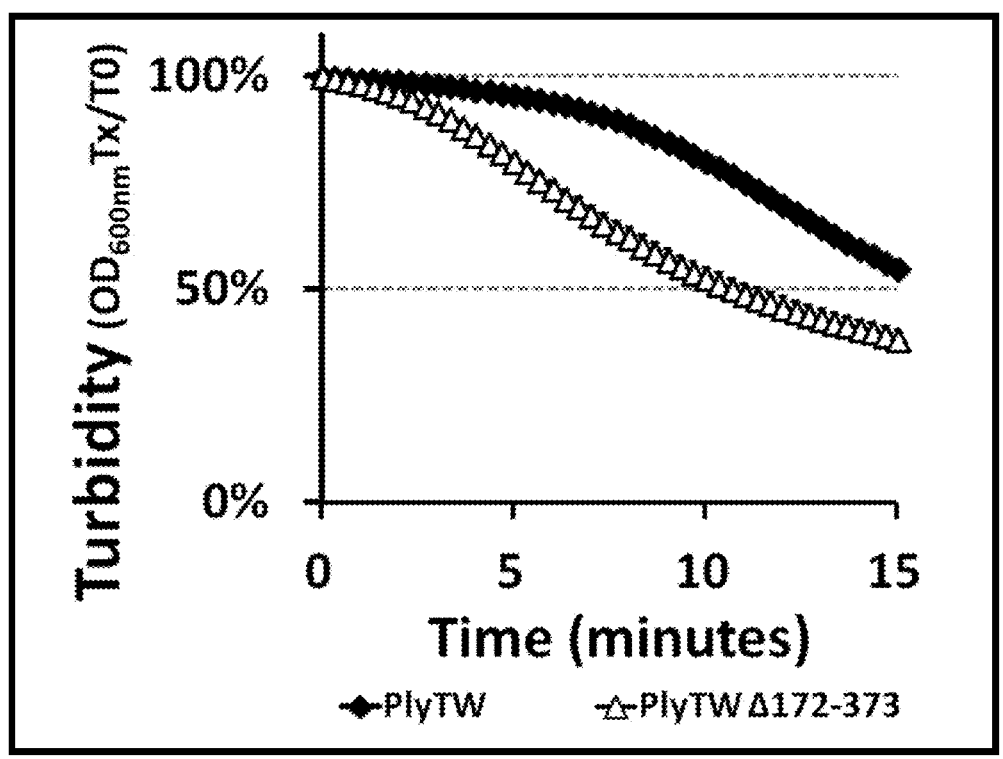
FIG. 5 depicts the 15 min turbidity reduction curves for each PlyTW derivative at 0.5 μM summarized in FIG. 1D: PlyTW (black diamonds), PlyTW 146' (black circles), PlyTW Δ146-373 (white squares), PlyTW Δ172-373 (white triangles) and buffer only (white circles). Each data point represents the average of 6 replicates for each 20 sec time point with standard deviation.

To determine the effect of divalent cations on the activity of PlyTW constructs, each protein was assayed in the presence of two fold serial dilutions of 0.5 mM of either $Ca^{2+}$, $Mg^{2+}$, $Mn^{2+}$, $Zn^{2+}$, or EDTA. Addition of $Ca^{2+}$ increased the activity of all PlyTW constructs, increasing the PlyTW lysin 4 fold (FIG. 4A), PlyTW 146', 6.5 fold (FIG. 4B), PlyTWΔ146-373, 8.2 fold (FIG. 4C), and PlyTWΔ172-373 increased minimally 2.8 fold, underestimated due to the upper limit of the assay (FIG. 4D). Neither $Mg^{2+}$ nor $Mn^{2+}$ had a significant effect on the turbidity lysis assay for any of the constructs tested. Addition of $Zn^{2+}$ or EDTA inhibited both the full length and the internal deletion constructs (FIGS. 4A, C, and D) with no detectable effect on PlyTW 146' potentially due to the low activity of the construct.

Example 5

Plate Lysis Assay

Figure 2:
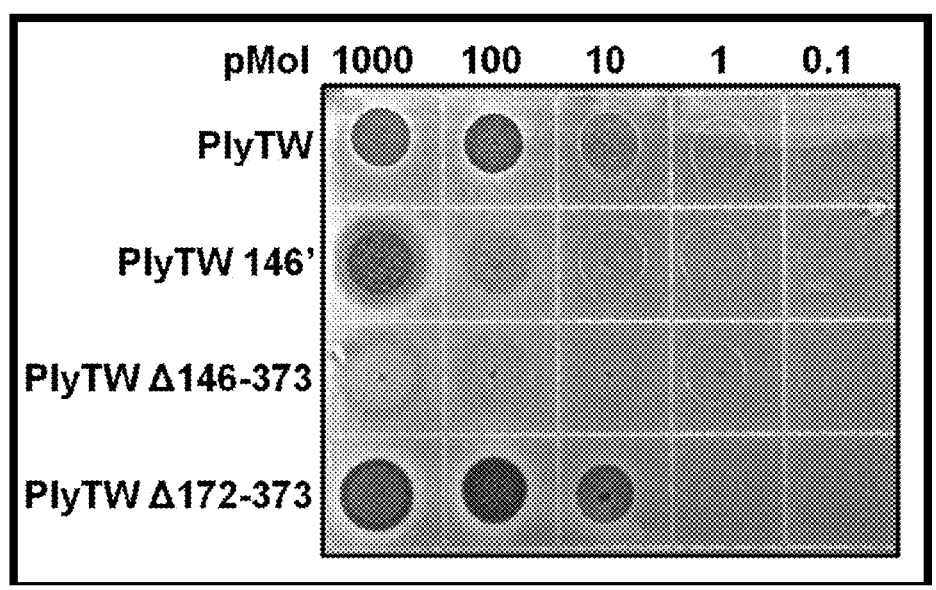
FIG. 2 depicts the activity of PlyTW constructs on *S. aureus* in the Plate Lysis Assay. Spots, 10 μl drops, containing serial 10 fold dilutions from 1 μmol of purified hydrolase in sterile SLB were spotted onto fresh lawns of *S. aureus* strain Newman. Plates were incubated overnight, then photographed.

The four highest activity PlyTW constructs were used for further analysis in the plate lysis assay. Each enzyme was tested for its ability to kill untreated, live bacteria (FIG. 2). Purified enzymes were serially diluted in saline lysis buffer (SLB; 150 mM NaCl, 10 mM Tris buffer, pH 7.5) to yield concentrations of 1000, 100, 10, 1 and 0.1 pmoles/10 μl. 10 μl of each dilution was then spotted onto a freshly plated, air-dried lawn of *S. aureus* Newman, allowed to air dry, and incubated overnight at 37° C. The following day, plates were evaluated visually and photographed.

The results from the plate lysis assay mimic the turbidity reduction assay results (FIG. 1D). Again, the CHAP domain alone (PlyTW 146') was sufficient to lyse live cells (demonstrating reduced lawn density at 100 pMol), but showed approximately 10 fold reduction in activity compared to full length PlyTW (reducing lawn density at 10 pMol). PlyTW Δ146-373 did not show enhanced activity at higher concentrations, but showed some lytic activity at a lower concentration (10 pMol) than the CHAP domain alone (PlyTW 146'). As in the turbidity reduction assay, the CHAP plus SH3b construct (PlyTW Δ172-373) shows enhanced activity over full length PlyTW, with strong lytic activity at 10 pMol.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated or recombinant nucleic acid encoding an antimicrobial peptidoglycan hydrolase polypeptide, wherein said polypeptide comprises a truncated Phage Twort (PlyTW) polypeptide having exolytic function and specificity for the peptidoglycan cell wall of staphylococcal bacteria, wherein said nucleic acid encodes a truncated endolysin-derived peptidoglycan hydrolase molecule having the sequence SEQ ID NO: 4, SEQ ID NO: 22 or SEQ ID NO: 24.

2. The nucleic acid of claim 1, wherein the truncated peptidoglycan hydrolase has endopeptidase activity and does not require a SH3b binding domain.

3. The nucleic acid of claim 1, wherein the truncated peptidoglycan hydrolase has endopeptidase activity, does not require amidase activity and requires a SH3b binding domain.

4. A construct comprising the nucleic acid of claim 1, wherein said nucleic acid is in operable linkage to a promoter that drives expression in a host cell.

5. A cloning vector comprising the construct of claim 4.

6. An expression vector comprising the construct of claim 4.

7. A process for transforming a host cell, comprising stably integrating the nucleic acid of claim 1 or the construct of claim 4 into the host cell.

8. An isolated host cell transformed with the nucleic acid according to claim 1.

9. An isolated host cell transformed with the construct according to claim 4.

10. The host cell of claim 8 or 9, wherein said host cell is a single-celled or lower or higher multi-celled organism into which the construct according to the invention can be introduced so as to produce an antimicrobial peptidoglycan hydrolase.

11. A method of making a recombinant peptidoglycan hydrolase protein, said method comprising steps:
   a. introducing into a host cell a nucleic acid or construct encoding a peptidoglycan hydrolase protein;
   b. culturing said cell under conditions suitable for expression of said protein;
   c. recovering the protein so expressed.

* * * * *